United States Patent
DeLuca et al.

(10) Patent No.: US 9,688,596 B2
(45) Date of Patent: Jun. 27, 2017

(54) SYNTHESIS AND BIOLOGICAL ACTIVITY OF 2-METHYLENE ANALOGS OF CALCITRIOL AND RELATED COMPOUNDS

(71) Applicant: Wisconsin Alumni Research Foundation, Madison, WI (US)

(72) Inventors: Hector F. DeLuca, Deerfield, WI (US); Izabela K. Sibilska, Warsaw (PL); Rafal R. Sicinski, Warsaw (PL); Lori A. Plum, Arena, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

(21) Appl. No.: 15/220,035

(22) Filed: Jul. 26, 2016

(65) Prior Publication Data

US 2017/0036977 A1 Feb. 9, 2017

Related U.S. Application Data

(60) Provisional application No. 62/201,341, filed on Aug. 5, 2015.

(51) Int. Cl.
| | | |
|---|---|---|
| *A23L 1/30* | (2006.01) | |
| *C07C 35/21* | (2006.01) | |
| *C07F 7/18* | (2006.01) | |
| *A61K 31/593* | (2006.01) | |

(52) U.S. Cl.
CPC ............ *C07C 35/21* (2013.01); *A61K 31/593* (2013.01); *C07F 7/1848* (2013.01); *C07C 2101/14* (2013.01); *C07C 2102/24* (2013.01)

(58) Field of Classification Search
None
See application file for complete search history.

(56) References Cited

U.S. PATENT DOCUMENTS

| | | |
|---|---|---|
| 6,846,811 B2 | 1/2005 | DeLuca et al. |
| 8,410,080 B1 | 4/2013 | DeLuca et al. |
| 2012/0322775 A1 | 12/2012 | DeLuca et al. |

OTHER PUBLICATIONS

Binderup, L.; Binderup. E.; Godtfredsen, W. O. Development of new vitamin D analogs. In: Feldman, D.; Glorieux, F. H.; Pike, J. W. (Eds.), Vitamin D: Academic Press, New York, 1997, 1027-1043.
Bouillon, R.; Okamura, W. H.; Norman, A. W. Structure-function relationships in the vitamin D endocrine system. Endocr. Rev. 1995, 16, 200-257.
Chen, Y.; Gao, L.-J.; Murad, I.; Verstuyf, A.; Verlinden, L.; Verboven, C.; Bouillon, R.; Viterbo, D.; Milanesio, M.; Van Haver, D.; Vandewalle, M.; De Clercq, P. J. Synthesis, biological activity, and conformational analysis of CD-ring modified trans-decalin 1α,25-dihydroxyvitamin D analogs. Org. Biomol. Chem. 2003, 1, 257-267.
Chiellini, G.; Grzywacz, P.; Plum, L. A.; Barycki, R.; Clagett-Dame, M.; DeLuca, H. F. Synthesis and biological properties of 2-methylene-19-nor-25-dehydro-1α-hydroxyvitamin D3-26,23-lactones-weak agonists. Bioorg. Med. Chem. 2008, 16, 8563-8573.
DeLuca, H. F. The development of a bone- and parathyroid-specific analog of vitamin D: 2-methylene-19-nor-(20S)-1α,25-dihydroxyvitamin D3. In: BoneKEy Reports, Article No. 514 2014.
DeLuca, H. F.; Bedale, W.; Binkley, N.; Gallagher, J. C.; Bolognese, M.; Peacock, M.; Aloia, J.; Clagett-Dame, M.; Plum, L. The vitamin D analogue 2MD increases bone turnover but not BMD in post-menopausal women with osteopenia: Results of a 1-year phase 2 double-blind, placebo-controlled, randomized clinical trial. J. Bone Miner. Res. 2011, 26, 538-545.
Desmaele, D.; Tanier, S. Nouvelle synthese du cycle a du 1S-hydroxycholecalciferol a partir de l'acide quinique. Tetrahedron Lett. 1985, 26, 4941-4944.
Glebocka, A.; Chiellini, G. A-Ring analogs of 1,25-dihydroxyvitamin D3. Arch. Biochem. Biophys. 2012, 523, 48-57.
Glebocka, A.; Sicinski, R. R.; Plum, L. A.; Clagett-Dame, M.; DeLuca, H. F. New 2-alkylidene 1α,25-dihydroxy-19-norvitamin D3 analogues of high intestinal activity: synthesis and biological evaluation of 2-(3'-alkoxypropylidene) and 2-(3'-hydroxypropylidene) derivatives. J. Med. Chem. 2006, 49, 2909-2920.
Gothelf, K. V.; Jorgensen, K. A. Asymmetric 1,3-dipolar cycloaddition reactions. Chem. Rev. 1998, 98, 863-909.
Haussler, M. R.; Whitfield, G. K.; Kaneko, I.; Haussler, C.A.; Hsieh, D.; Hsieh, J. C.; Jurutka, P. W. Molecular mechanisms of vitamin D action. Calcif. Tissue Int. 2013, 92, 77-98.
Hayashi, R.; Fernández, S.; Okamura, W. H. An 8π electron electrocyclization leading to a 9,19-methano-bridged analogue of 1α,25-dihydroxyvitamin D3. Org. Lett. 2002, 4, 851-854.
Jones, G.; Strugnell, S. A.; DeLuca, H. F. Current understanding of the molecular actions of vitamin D. Physiol. Rev. 1998, 78, 1193-1231.
Ke, H. Z.; Qi, H.; Crawford, D. T.; Simmons, H. A.; Xu, G.; Li, M.; Plum, L.; Clagett-Dame, M.; DeLuca, H. F.; Thompson, D. D.; Brown, T. A. A new vitamin D analog, 2MD, restores trabecular and cortical bone mass and strength in ovariectomized rats with established osteopenia. J. Bone Miner. Res. 2005, 20, 1742-1755.
Maestro, M. A.; Sardina, F. J.; Castedo, L.; Mourino, A. J. Org. Chem. 1991, 56, 3582-3587.
Mascareñas, J. L.; Sarandeses, L. A.; Castedo, L.; Mouriño, A. Passadium-catalysed coupling of vinyl triflates with enynes and its application to the synthesis of 1α,25-dihydroxyvitamin D3. Tetrahedron, 1991, 47, 3485-3498.

(Continued)

*Primary Examiner* — Jeffrey S Lundgren
*Assistant Examiner* — Stephanie Springer
(74) *Attorney, Agent, or Firm* — Andrus Intellectual Property Law, LLP

(57) ABSTRACT

Disclosed are 2-methylene analogs of vitamin $D_3$ and related compounds, their biological activities, and various pharmaceutical uses for these analogs. Particularly disclosed are 1α-hydroxy-2-methylene-vitamin $D_3$, (20S)-1α-hydroxy-2-methylene-vitamin $D_3$, and (5E)-1α,25-dihydroxy-2-methylene-vitamin $D_3$, their biological activities, and various pharmaceutical uses for these compounds including methods of treating and/or preventing bone diseases and disorders.

7 Claims, 13 Drawing Sheets

(56) References Cited

OTHER PUBLICATIONS

Norman, A. W. Vitamin D, the calcium homeostatic hormone. Academic Press, New York, 1979.

Okamura, W. H.; Zhu, G. D. Chemistry and design: structural biology of vitamin D action. In: Feldman, D.; Glorieux, F. H.; Pike, J. W. (Eds.), Vitamin D: Academic Press, New York, 1997, 937-971.

Padwa, A., Pearson, W. H., Eds. Synthetic applications of 1,3-dipolar cycloaddition chemistry toward heterocycles and natural products; An Interscience Publication John Wiley & Sons, Inc. Hoboken, NJ, 2003; vol. 59, p. 539.

Plum, L. A.; Fitzpatrick, L. A.; Ma, X.; Binkley, N.; Zella, J. B.; Clagett-Dame, M.; DeLuca, H. F. 2MD, a new anabolic agent for osteoporosis treatment. Osteoporos. Int. 2006, 17, 704-715.

Shevde, N. K.; Plum, L. A.; Clagett-Dame, M.; Yamamoto, H.; Pike, J. W.; DeLuca, H. F. A potent analog of 1α,25-dihydroxyvitamin D3 selectively induces bone formation. Proc. Natl. Acad. Sci. USA 2002, 99, 13487-13491.

Sibilska, I. K.; Barycka, K. M.; Sicinski, R. R.; Plum, L. A.; DeLuca ,H. F. 1-Desoxy analog of 2MD: synthesis and biological activity of (20S)-25-hydroxy-2-methylene-19-norvitamin D3. J. Steriod Biochem. Mol. Biol. 2010, 121, 51-55.

Sibilsk, I. K.; Sicinski, R. R.; Ochalek J. T.; Plum, L. A.; DeLuca, H.F. Synthesis and Biological Activity of 25-hydroxy-2-methylene-vitamin D analogues monohydroxylated in the A-ring. J. Med. Chem. 2014, 57, 8319-8331.

Sibilska, I. K.; Sicinski, R. R.; Plum, L. A.; DeLuca, H. F. Synthesis and biological activity of 25-hydroxy-2-methylene-vitamin D3 compounds. J. Steroid Biochem. Mol. Biol. 2013, 136, 17-22.

Sibilska, I. K.; Szybinski, M.; Sicinski, R. R.; Plum, L. A.; DeLuca, H. F. Highly potent 2-methylene analogs of 1α,25-dihydroxyvitamin D3: Synthesis and biological evaluation. J. Steroid Biochem. Mol. Biol. 2013, 136, 17-22.

Sicinski, R. R. 2-Alkylidene analogs of 19-nor-1α,25-(OH)2D3: Synthesis and biological activity. Polish J. Chem. 2006, 80, 573-585.

Sicinski, R. R.; Perlman, K. L.; DeLuca, H. F. Synthesis and biological activity of 2-hydroxy and 2-alkoxy analogues of 1α,25-dihydroxy-19-norvitamin D3. J. Med. Chem. 1994, 37, 3730-3738.

Sicinski, R. R.; Prahl, J. M.; Smith, C. M.; DeLuca, H. F. New 1α,25-dihydroxy-19-norvitamin D3 compounds of high biological activity: synthesis and biological evaluation of 2-hydroxymethyl, 2-methyl and 2-methylene analogues. J. Med. Chem. 1998, 41, 4662-4674.

Suda, T.; DeLuca, H. F.; Tanaka, Y. Biological activity of 25-hydroxyergocalciferol in rats. J. Nutr. 1970, 100, 1049-1052.

Verloop, A.; Koevoet, A. L.; Van Moorselaar, R.; Havinga, E. Studies on vitamin D and related compounds IX: Remarks on the iodine-catalyzed isomerisations of vitamin D and related compounds. Rec. Trav. Chim. 1959, 78, 1004-1014.

Yamamoto, H.; Shevde, N. K.; Warrier, A.; Plum, L. A.; DeLuca, H. F.; Pike, J. W.; 2-Methylene-19-nor-(20S)-1,25-dihydroxyvitamin D3 potently stimulates gene-specific DNA binding of the vitamin D receptor in osteoblasts. J. Biol. Chem. 2003, 278, 31756-31765.

International Search Report for PCT/US2016/044067 dated Oct. 7, 2016.

Written Opinion of the International Searching Authority for PCT/US2016/044067 dated Oct. 7, 2016.

SYNTHESIS AND BIOLOGICAL ACTIVITY OF 2-METHYLENE ANALOGS OF CALCITRIOL AND RELATED COMPOUNDS

CROSS-REFERENCE TO RELATED PATENT APPLICATIONS

The present application claims the benefit of priority under 35 U.S.C. §119(e) to U.S. Provisional Patent Application No. 62/201,341, filed on Aug. 5, 2015, the content of which is incorporated herein by reference in its entirety.

BACKGROUND

The field of the invention relates to vitamin D compounds, and more particularly to the synthesis and biological activity of 2-methylene analogs of calcitriol and related compounds.

The natural hormone, $1\alpha,25$-dihydroxyvitamin $D_3$ and its analog in the ergosterol series, i.e., $1\alpha,25$-dihydroxyvitamin $D_2$, are known to be highly potent regulators of calcium homeostasis in animals and humans, and their activity in cellular differentiation has also been established. (See Ostrem et al., Proc. Natl. Acad. Sci. USA, 84, 2610 (1987)). Many structural analogs of these metabolites have been prepared and tested, including $1\alpha$-hydroxyvitamin $D_3$, $1\alpha$-hydroxyvitamin $D_2$, various side-chain homologated analogs, and fluorinated analogs. Some of these vitamin D analogs exhibit biological activities that differ from the biological activities of the native vitamin D compounds, including decreased or increased biological activity related to calcium regulation and cell differentiation as compared to the native vitamin D compounds. The difference in biological activities exhibited by vitamin D analogs may be exploited in the treatment of a variety of diseases such as renal osteodystrophy, vitamin D-resistant rickets, osteoporosis, psoriasis, and certain malignancies, where some of the biological activities of vitamin D compounds are desirable, but other of the biological activities of vitamin D compounds are not desirable.

One class of vitamin D analogs, i.e., the so called 19-nor-vitamin D compounds, is characterized by the replacement of the A-ring exocyclic methylene group (carbon 19), typical of the vitamin D system, by two hydrogen atoms. Several 19-nor-analogs (e.g., $1\alpha,25$-dihydroxy-19-nor-vitamin $D_3$) exhibit a selective, biological activity profile characterized by a high potency in inducing cellular differentiation, and a low potency in inducing calcium-mobilizing activity. Thus, some of these compounds are potentially useful as therapeutic agents for the treatment of malignancies or the treatment of various skin disorders. Methods for synthesizing such 19-nor-vitamin D analogs have been described. (See Perlman et al., Tetrahedron Lett. 31, 1823 (1990); Perlman et al., Tetrahedron Lett. 32, 7663 (1991), and DeLuca et al., U.S. Pat. No. 5,086,191).

Vitamin $D_3$ analogs substituted at carbon 2 (C-2) also have been synthesized, including compounds substituted at C-2 with: hydroxy or alkoxy groups (DeLuca et al., U.S. Pat. No. 5,536,713); 2-alkyl groups (DeLuca et al., U.S. Pat. No. 5,945,410); and 2-alkylidene groups (DeLuca et al., U.S. Pat. No. 5,843,928). Like the 19-nor analogs, these compounds also exhibit selective, biological activity profiles. In particular, U.S. Pat. No. 5,843,928 discloses a (20S)-$1\alpha,25$-dihydroxy-2-methylene-19-nor-vitamin $D_3$ analog otherwise referred to as "2MD." Studies of these analogs indicate that binding sites in vitamin D receptors can accommodate different substituents at C-2 in the synthesized vitamin D analogs.

Additional vitamin D analogs have been synthesized and tested, including analogs which are characterized by the presence of a methylene substituent at carbon 2 (C-2), a hydroxyl group at both carbon 1 (C-1) and carbon 3 (C-3), and a shortened side chain attached to carbon 20 (C-20). (See DeLuca et al., U.S. Pat. No. 6,566,352, disclosing $1\alpha$-hydroxy-2-methylene-19-nor-pregnacalciferol; DeLuca et al., U.S. Pat. No. 6,579,861, disclosing $1\alpha$-hydroxy-2-methylene-19-nor-homopregnacalciferol; and DeLuca et al., U.S. Pat. No. 6,627,622, disclosing $1\alpha$-hydroxy-2-methylene-19-nor-bishomopregnacalciferol). These analogs exhibit a relatively high binding activity to vitamin D receptors and a relatively high cell differentiation activity, but little if any calcemic activity as compared to $1\alpha,25$-dihydroxyvitamin $D_3$.

The biological activities of all of these analogs make them excellent candidates for a variety of pharmaceutical uses. Bone diseases such as osteoporosis, skin disorders such as psoriasis, cancers such as leukemia, and cosmetic conditions such as wrinkles are just some of the applications proposed for such compounds.

However, although a large number of vitamin D analogs exist, new analogs that may be utilized in therapeutic methods are desirable. Here, the inventors describe further vitamin D analogs.

SUMMARY

Disclosed are 2-methylene vitamin $D_3$ compounds, their biological activities, and various pharmaceutical uses for these compounds. These new vitamin D compounds are analogs of calcitriol and related compounds having a methylene group at the carbon 2 position (C-2), a methylene group at the carbon 4 position (C-4) (i.e. in the case of a 5E configuration), or a methylene group at the carbon 10 position (C-10) (i.e. in the case of a 5Z configuration), a hydroxyl group at the carbon 1 position (C-1) and the carbon 3 position (C-3), and optionally a hydroxyl group at the carbon 25 position (C-25). Specific members of this group of compounds may be referred to herein, especially in the description of their synthesis herein and the schemes, as $1\alpha,25$-dihydroxy-2-methylene-vitamin $D_3$ (otherwise referred to as "2EG-R"), (20S)-$1\alpha,25$-dihydroxy-2-methylene-vitamin $D_3$ (otherwise referred to as "2EG-S"), $1\alpha$-hydroxy-2-methylene-vitamin $D_3$ (otherwise referred to as "Des25-2EG-R"), (20S)-$1\alpha$-hydroxy-2-methylene-vitamin $D_3$ (otherwise referred to as "Des25-2EG-S"), (5E)-$1\alpha,25$-dihydroxy-2-methylene-vitamin $D_3$ (otherwise referred to as "T-2EG-R"), and (5E,20S)-$1\alpha,25$-dihydroxy-2-methylene-vitamin $D_3$ (otherwise referred to as "T-2EG-S").

Structurally these 2-methylene vitamin $D_3$ analogs are characterized by the general formula I or II shown below:

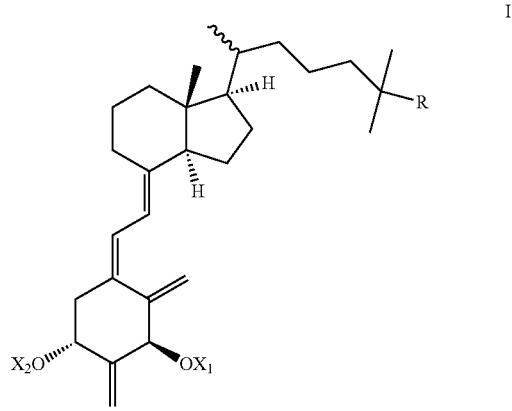

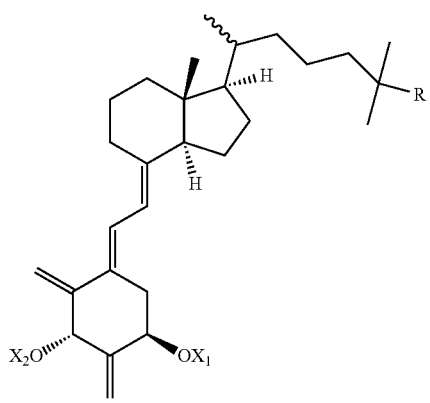

where R is hydrogen or OH; and $X_1$, and $X_2$, which may be the same or different, are each selected from hydrogen or a hydroxy-protecting group.

One disclosed analog is 1α,25-dihydroxy-2-methylene-vitamin $D_3$, otherwise referred to as "2EG-R", which has the following formula Ia:

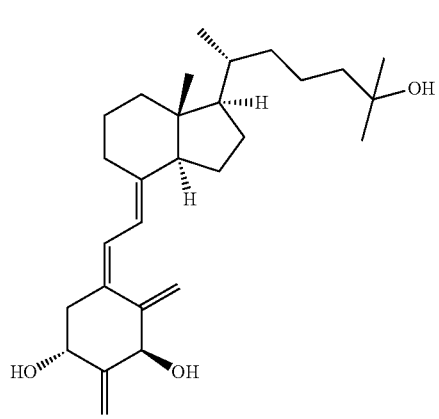

Another disclosed analog is (20S)-1α,25-dihydroxy-2-methylene-vitamin $D_3$, otherwise referred to as "2EG-S", which has the following formula Ib:

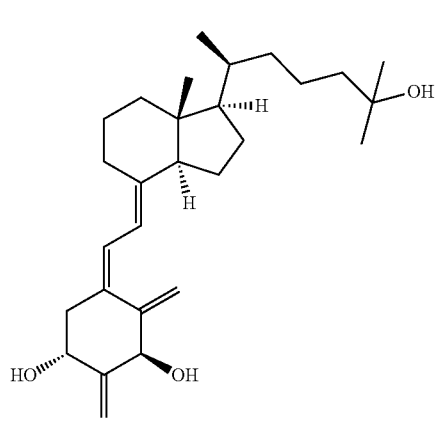

Another disclosed analog is 1α-hydroxy-2-methylene-vitamin $D_3$, otherwise referred to as "Des25-2EG-R", which has the following formula Ic:

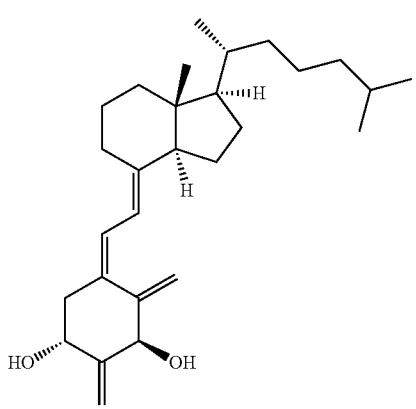

Another disclosed analog is (20S)-1α-hydroxy-2-methylene-vitamin $D_3$, otherwise referred to as "Des25-2EG-S", which has the following formula Id:

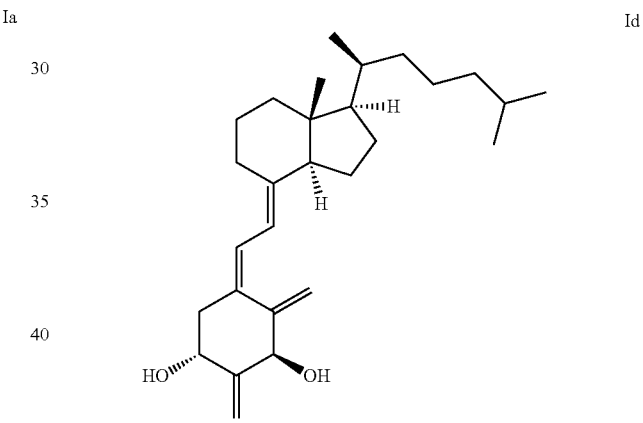

Another disclosed analog is (5E)-1α,25-dihydroxy-2-methylene-vitamin $D_3$, otherwise referred to as "T-2EG-R", which has the following formula IIa:

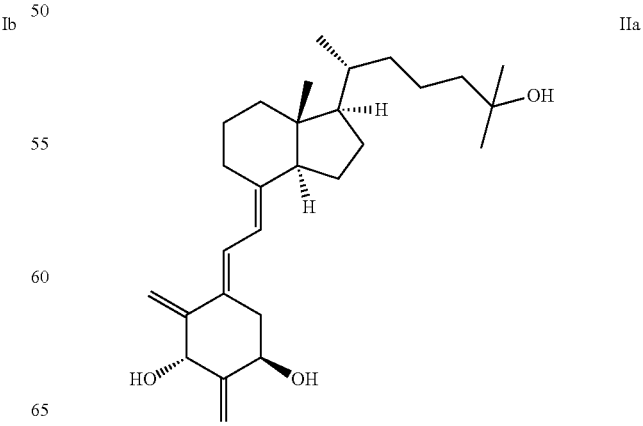

Another disclosed analog is (5E,20S)-1α,25-dihydroxy-2-methylene-vitamin D$_3$, otherwise referred to as "T-2EG-S", which has the following formula IIb:

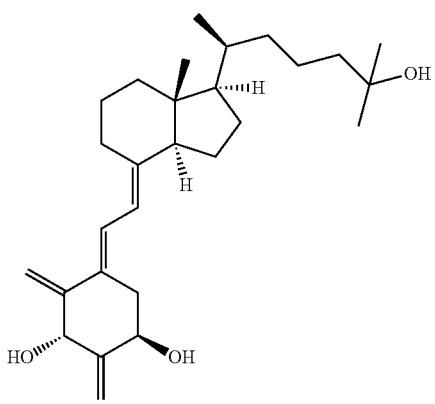

IIb

Also disclosed herein are compounds that may be utilized as precursors for preparing the 2-methylene analogs of calcitriol and related compounds disclosed herein. The precursor compounds may have a formula III:

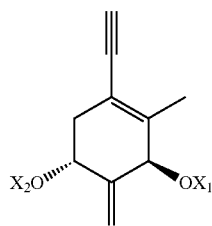

III wherein $X_1$, and $X_2$, which may be the same or different, are each selected from hydrogen or a hydroxy-protecting group.

As described herein, these compounds exhibit a desired, and highly advantageous pattern of biological activity. The compounds may be utilized in methods for treating and/or preventing diseases or disorders associated with vitamin D activity in a patient in need thereof. In some embodiments, the compounds disclosed herein may be utilized in methods for treating and/or preventing bone diseases and disorders, which may include, metabolic bone diseases and disorders where an increase in bone mass is desirable such as osteoporosis (e.g., senile osteoporosis, postmenopausal osteoporosis, steroid-induced osteoporosis, and low bone-turnover osteoporosis), osteopenia, and osteomalacia. The disclosed compounds also may be administered in methods for increasing bone strength in a patient.

In other embodiments, the compounds disclosed herein may be utilized in methods for treating and/or preventing skin diseases, disorders, and conditions in a patient in need thereof. These may include, but are not limited to psoriasis, acne, lack of adequate skin firmness, lack of adequate dermal hydration, and insufficient sebum secretion.

In further embodiments, the compounds disclosed herein may be utilized in methods for treating and/or preventing cell proliferative diseases or disorders such as cancer in a patient in need thereof. These may include, but are not limited to leukemia, colon cancer, breast cancer, skin cancer, and prostate cancer.

In even further embodiments, the compounds disclosed herein may be utilized in methods for treating and/or preventing autoimmune diseases and disorders in a patient in need thereof. These may include, but are not limited to multiple sclerosis, diabetes mellitus, lupus, host versus graft reaction, and rejection of transplants.

In even further embodiments, the compounds disclosed herein may be utilized in methods for treating and/or preventing inflammatory diseases. These may include, but are not limited to rheumatoid arthritis, asthmas, and inflammatory bowel diseases. The compounds may be utilized specifically in methods of treating or preventing inflammatory bowel diseases that include Crohn's disease and ulcerative colitis.

In even further embodiments, the compounds disclosed herein may be utilized in methods for treating and/or preventing obesity, inhibiting adipocyte differentiation, inhibiting SCD-1 gene transcription, and/or reducing body fat.

In even further embodiments, the compounds disclosed herein may be utilized in methods for treating and/or preventing secondary hyperparathyroidism, for example, secondary hyperparathryoidism of renal osteodystrophy.

DETAILED DESCRIPTION

Figure 1:
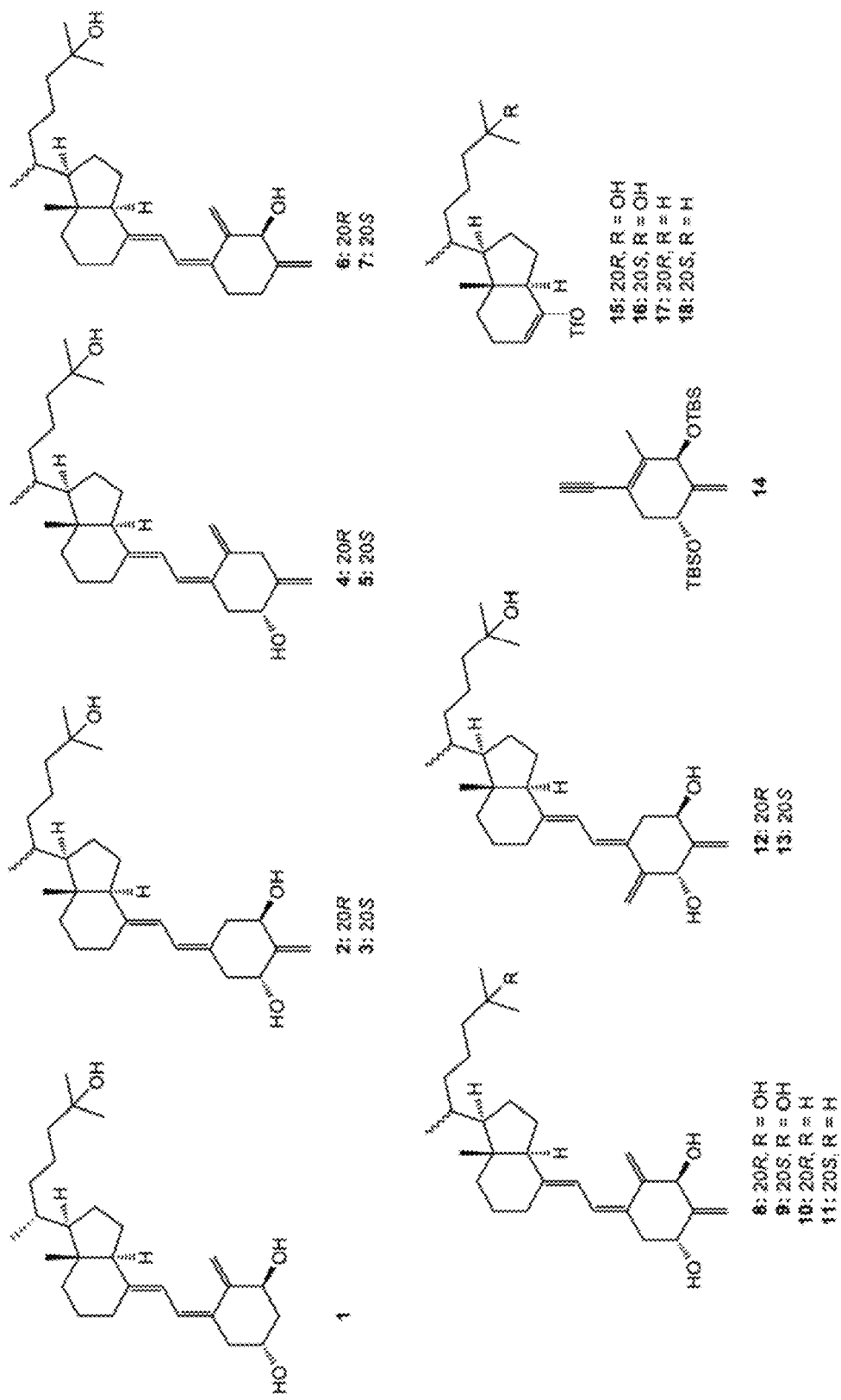
FIG. 1. Chemical structure of 1α,25-dihydroxyvitamin D$_3$ (calcitriol, 1), the previously synthesized 2-methylene compounds 2-7, 2-methylene calcitriol analogs described in this work 8-13, and the building blocks for their synthesis.
Figure 2:
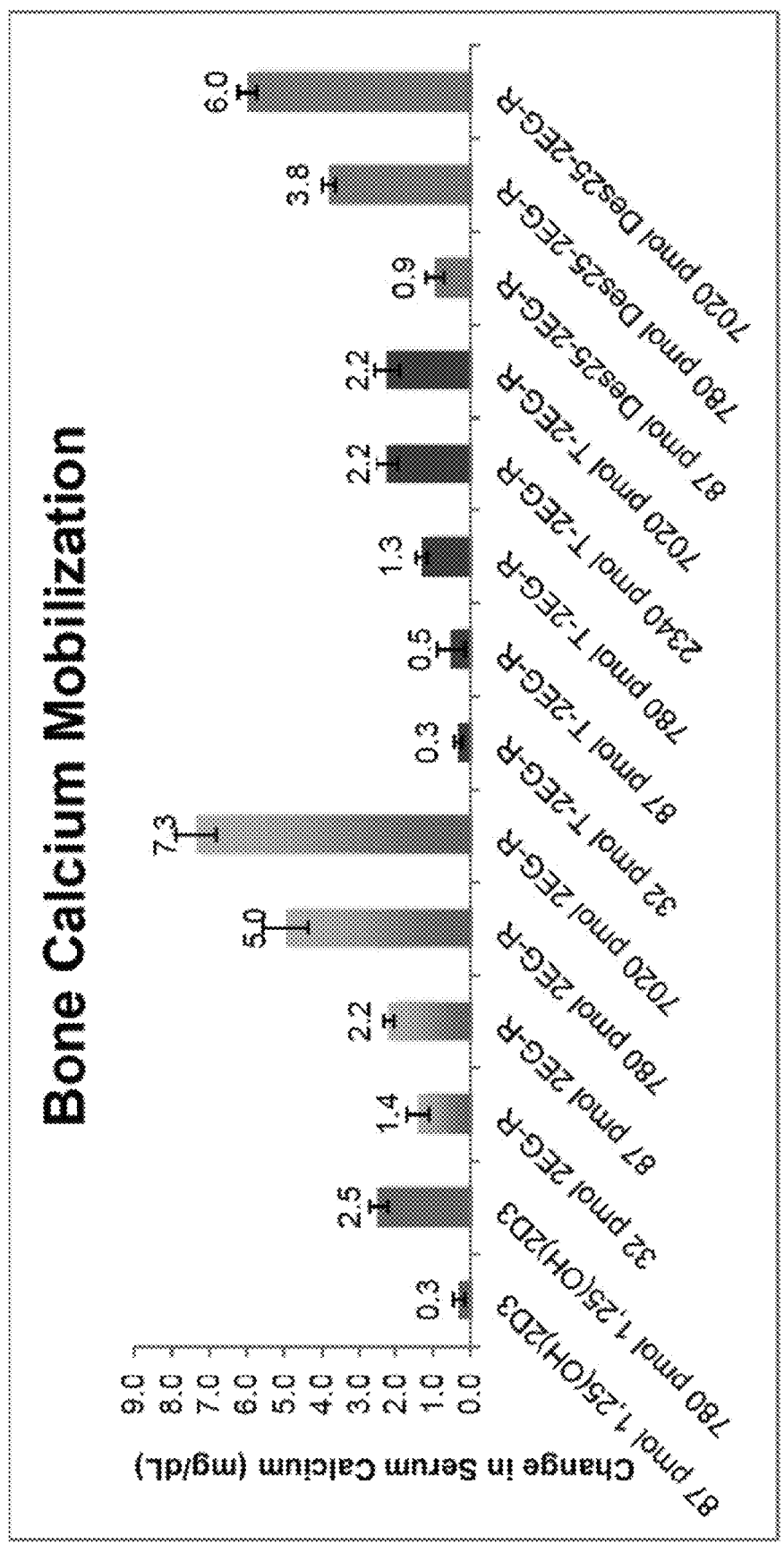
FIG. 2. Bone calcium mobilization activity of 1α,25-(OH)$_2$D$_3$ (1), the synthesized 2-methylene calcitriol analogs 8, 10 and 12, and 2-methylene analog of 1α-OH-D$_3$ (10).
Figure 3:
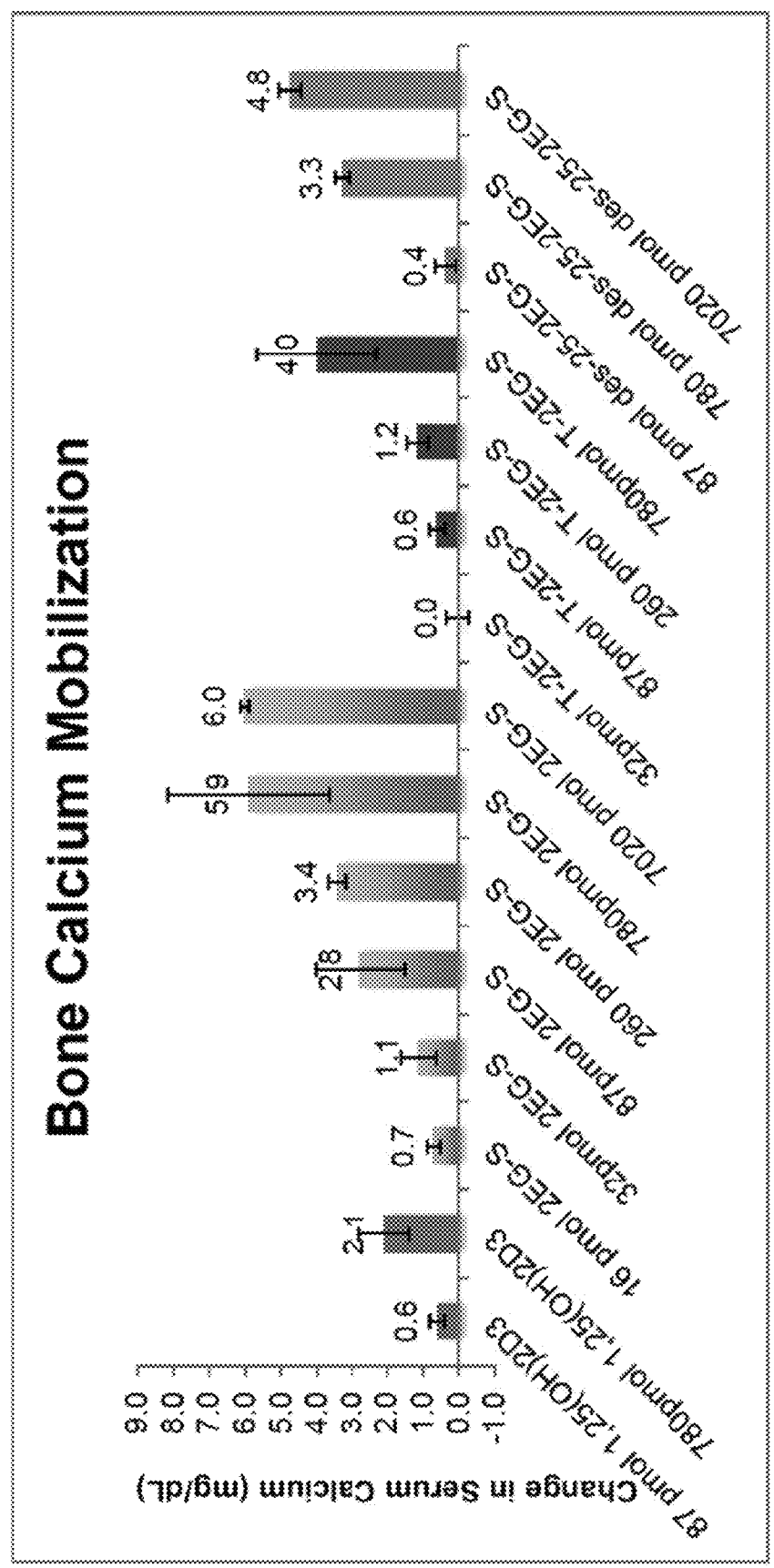
FIG. 3. Bone calcium mobilization activity of 1α,25-(OH)$_2$D$_3$ (1), the synthesized 2-methylene calcitriol analogs 9, 11 and 13, and 2-methylene analog of (20S)-1α-OH-D$_3$ (11).
Figure 4:
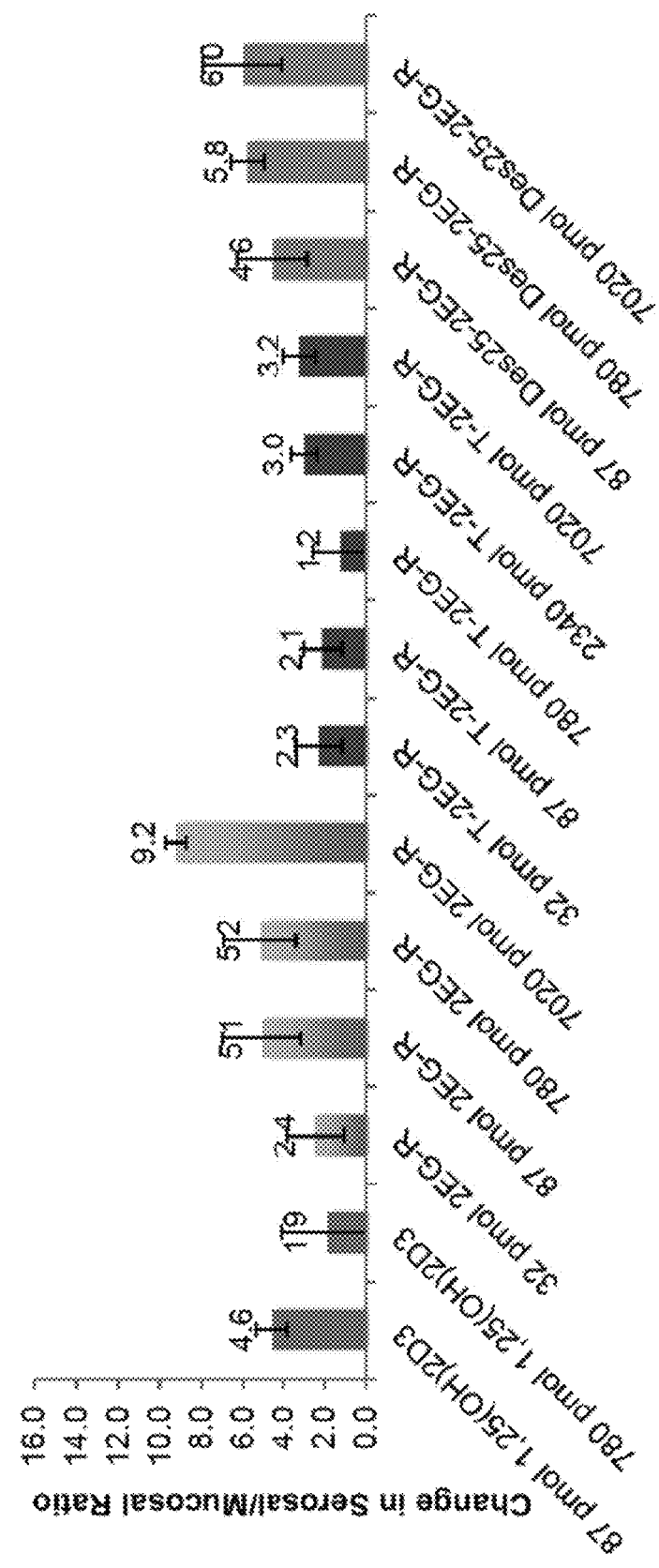
FIG. 4. Intestinal calcium transport activity of 1α,25-(OH)$_2$D$_3$ (1), the synthesized 2-methylene calcitriol analogs 8, 10 and 12, and 2-methylene analog of 1α-OH-D$_3$ (10).
Figure 5:
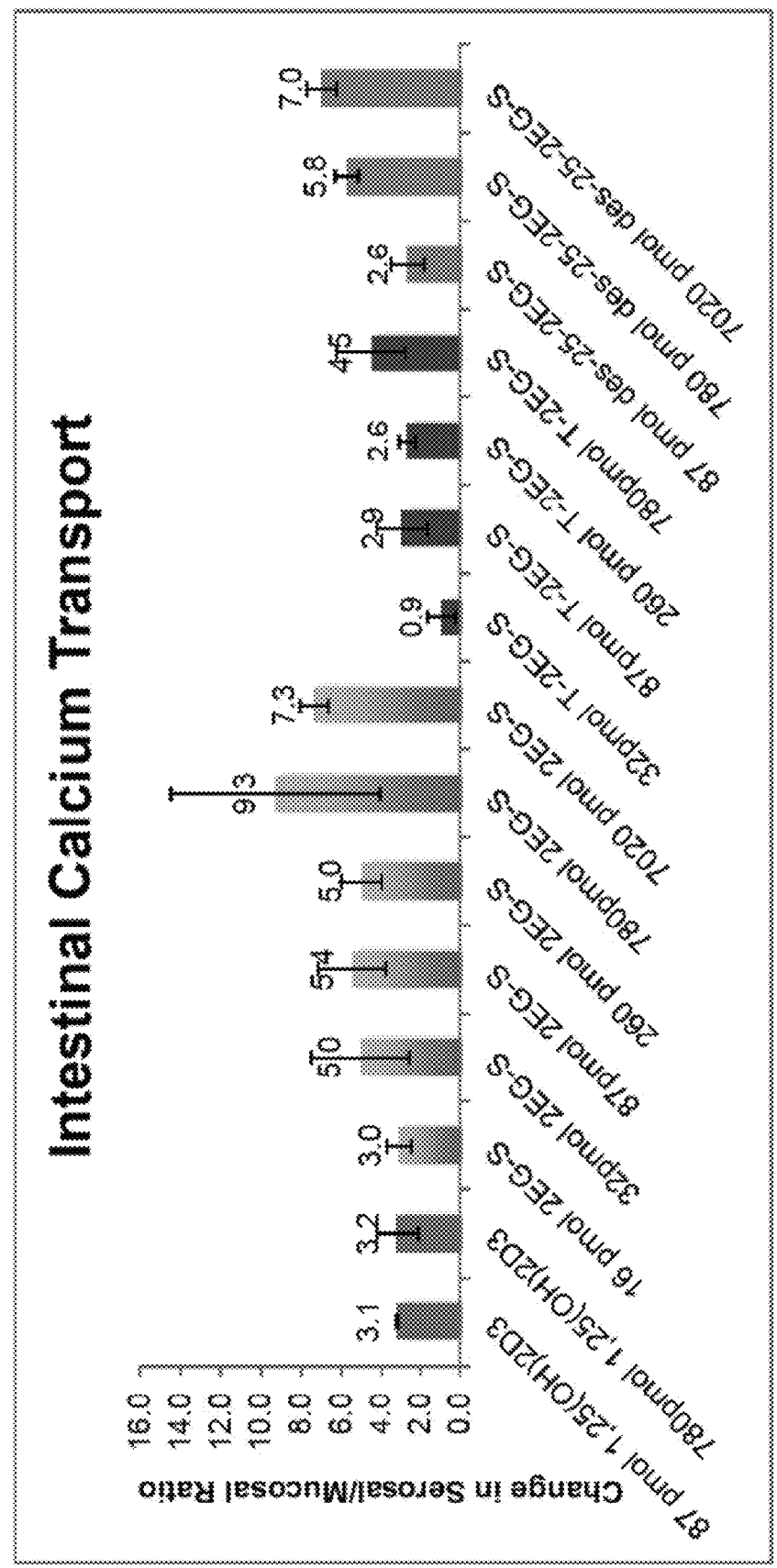
FIG. 5. Intestinal calcium transport activity of 1α,25-(OH)$_2$D$_3$ (1), the synthesized 2-methylene calcitriol analogs 9, 11 and 13, and 2-methylene analog of (20S)-1α-OH-D$_3$ (11).
Figure 6:
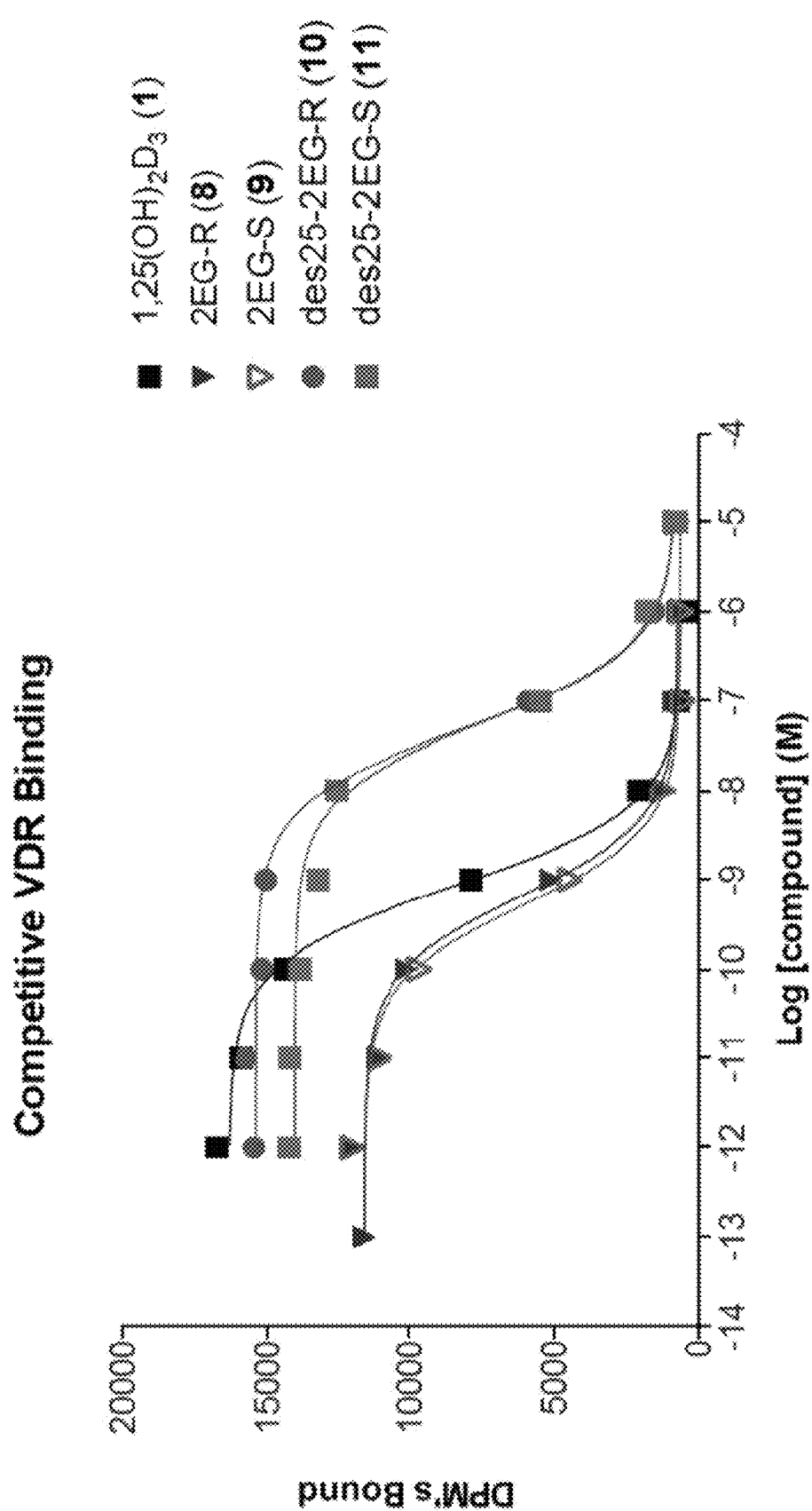
FIG. 6. Competitive binding of 1α,25-(OH)$_2$D$_3$ (1) and the synthesized vitamin D analogs 8-11.
Figure 7:
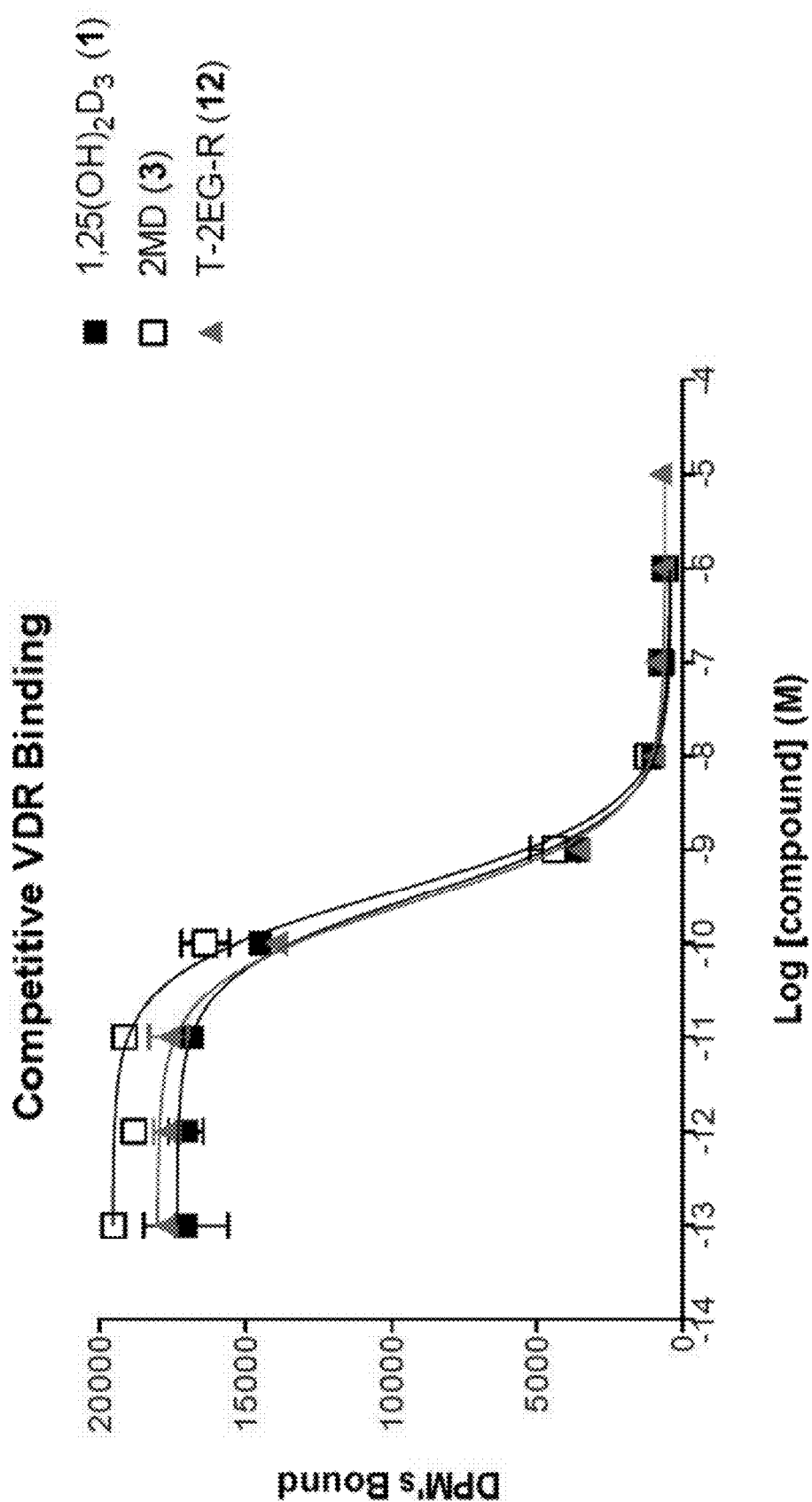
FIG. 7. Competitive binding of 1α,25-(OH)$_2$D$_3$ (1), 2MD (3) and the synthesized vitamin D analog 12.
Figure 8:
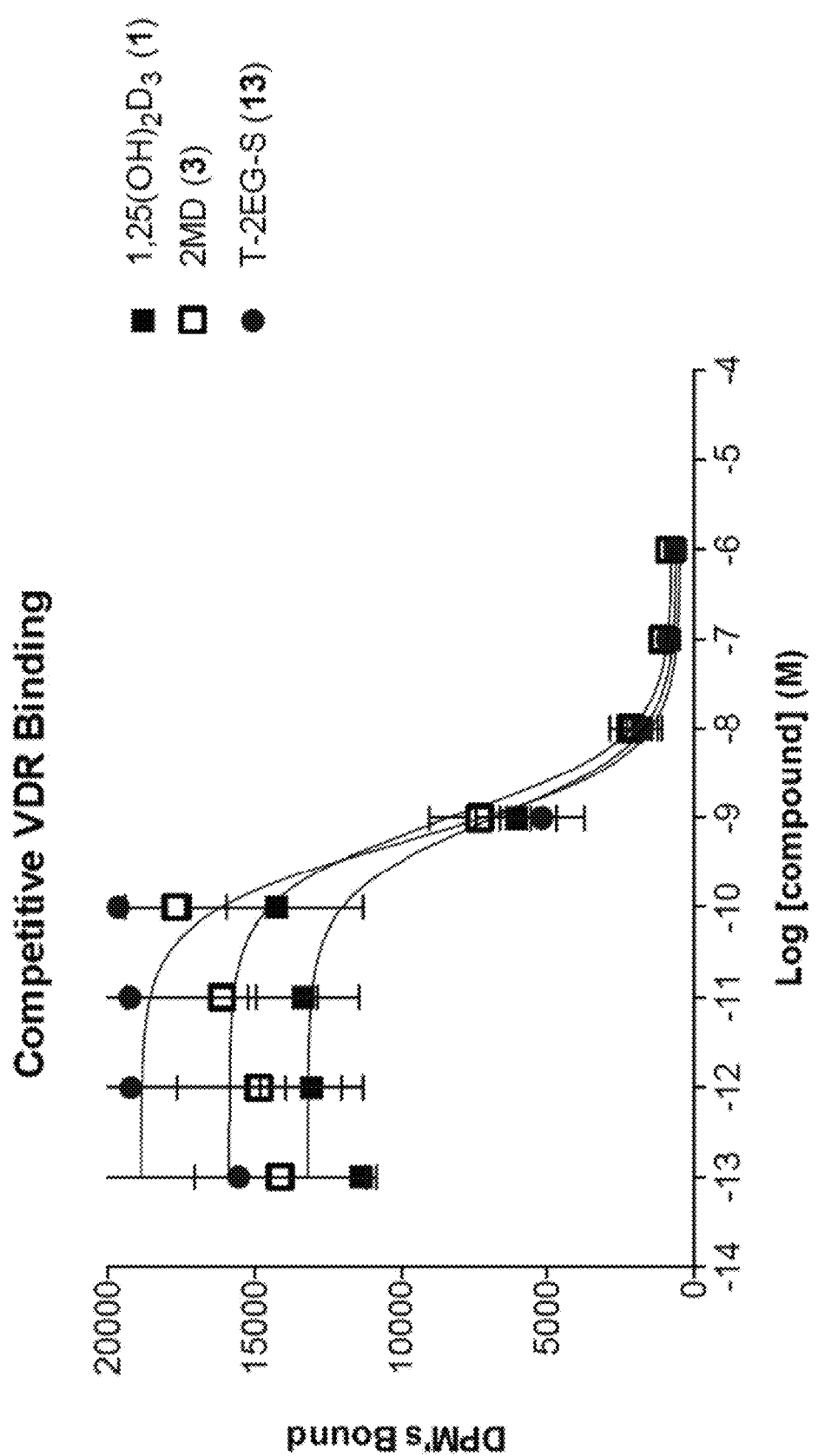
FIG. 8. Competitive binding of 1α,25-(OH)$_2$D$_3$ (1), 2MD (3) and the synthesized vitamin D analog 13.
Figure 9:
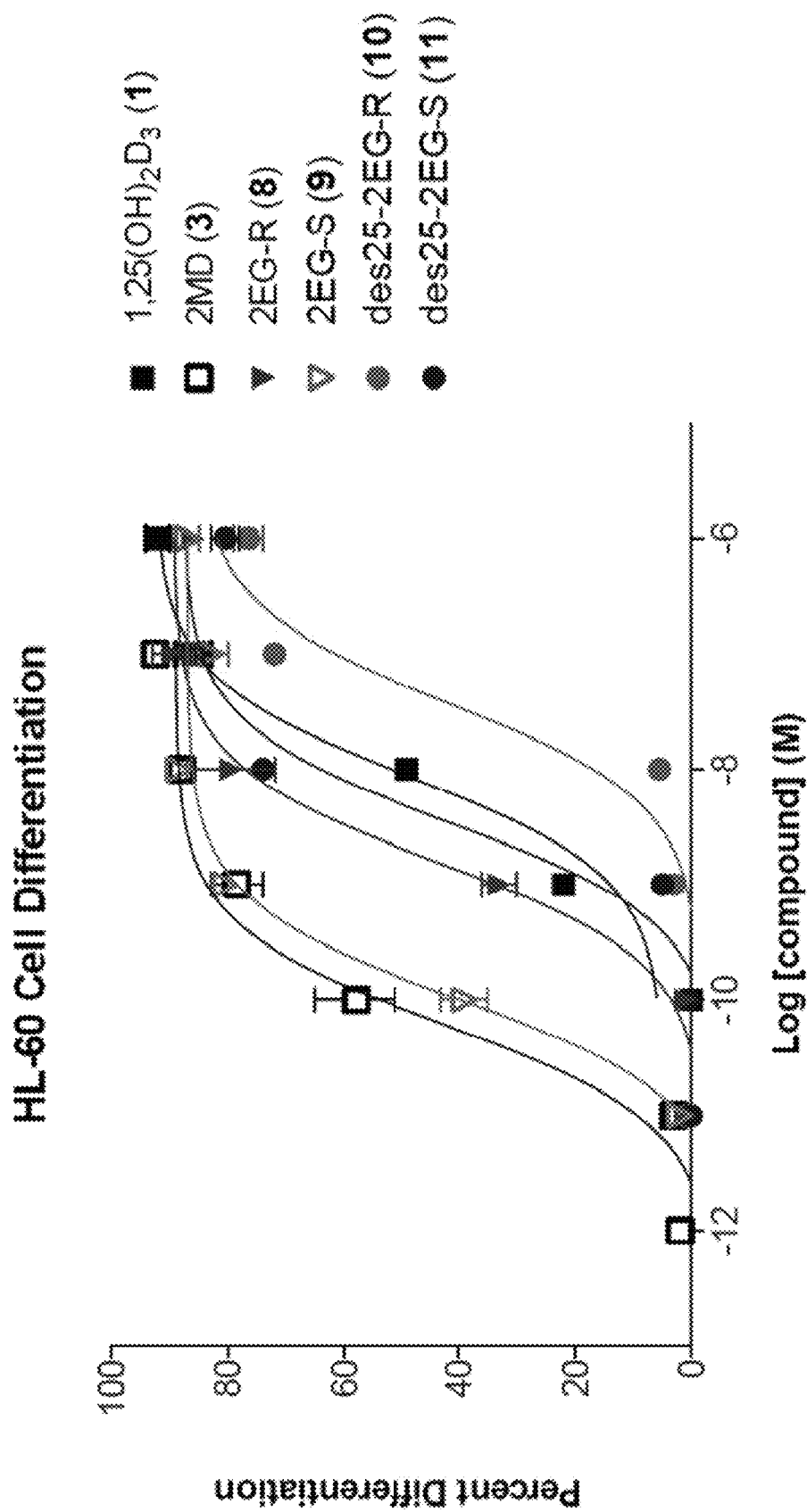
FIG. 9. Differentiation activity of 1α,25-(OH)$_2$D$_3$ (1), 2MD (3) and the synthesized vitamin D analogs 8-11.
Figure 10:
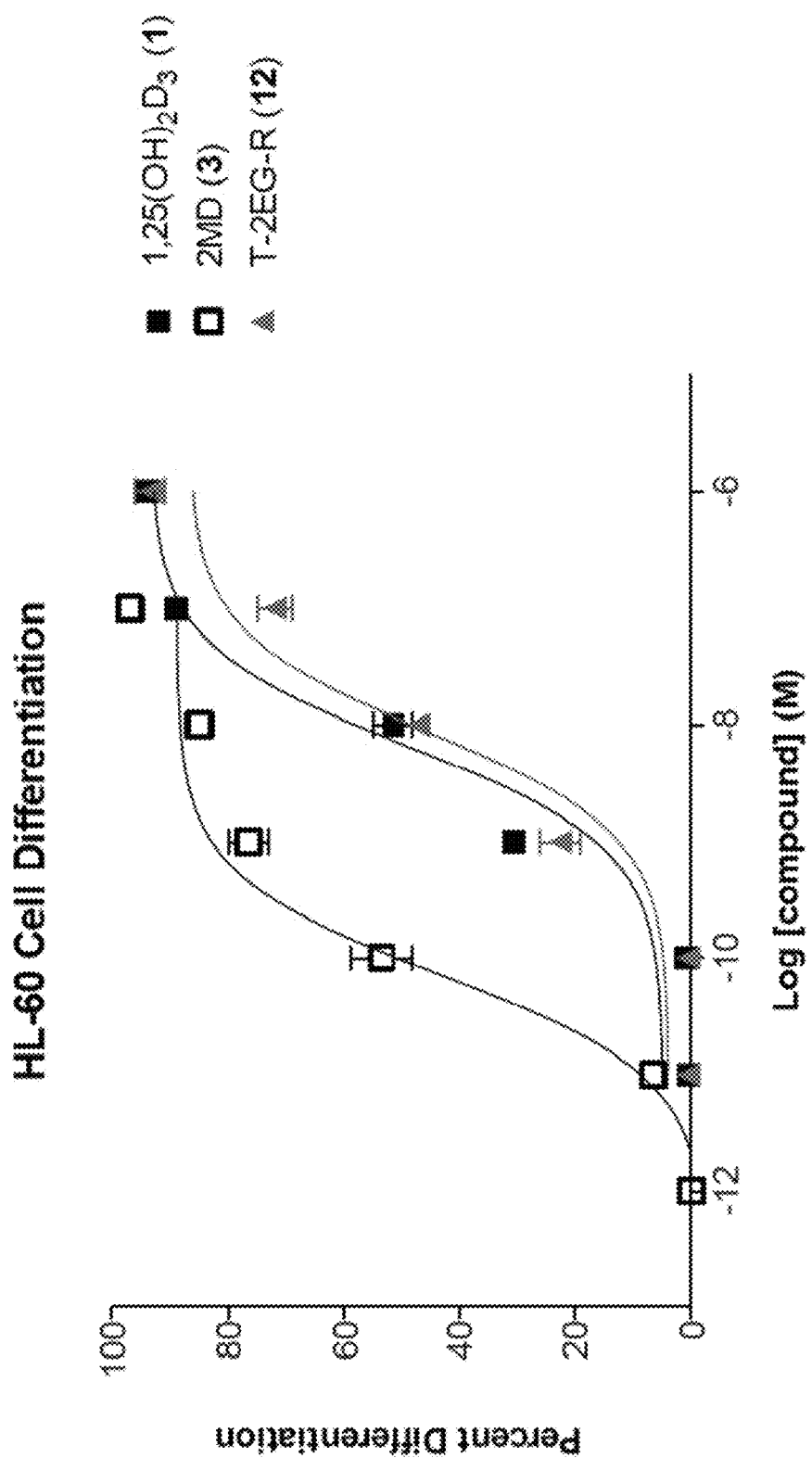
FIG. 10. Differentiation activity of 1α,25-(OH)$_2$D$_3$ (1), 2MD (3) and the synthesized vitamin D analog 12.
Figure 11:
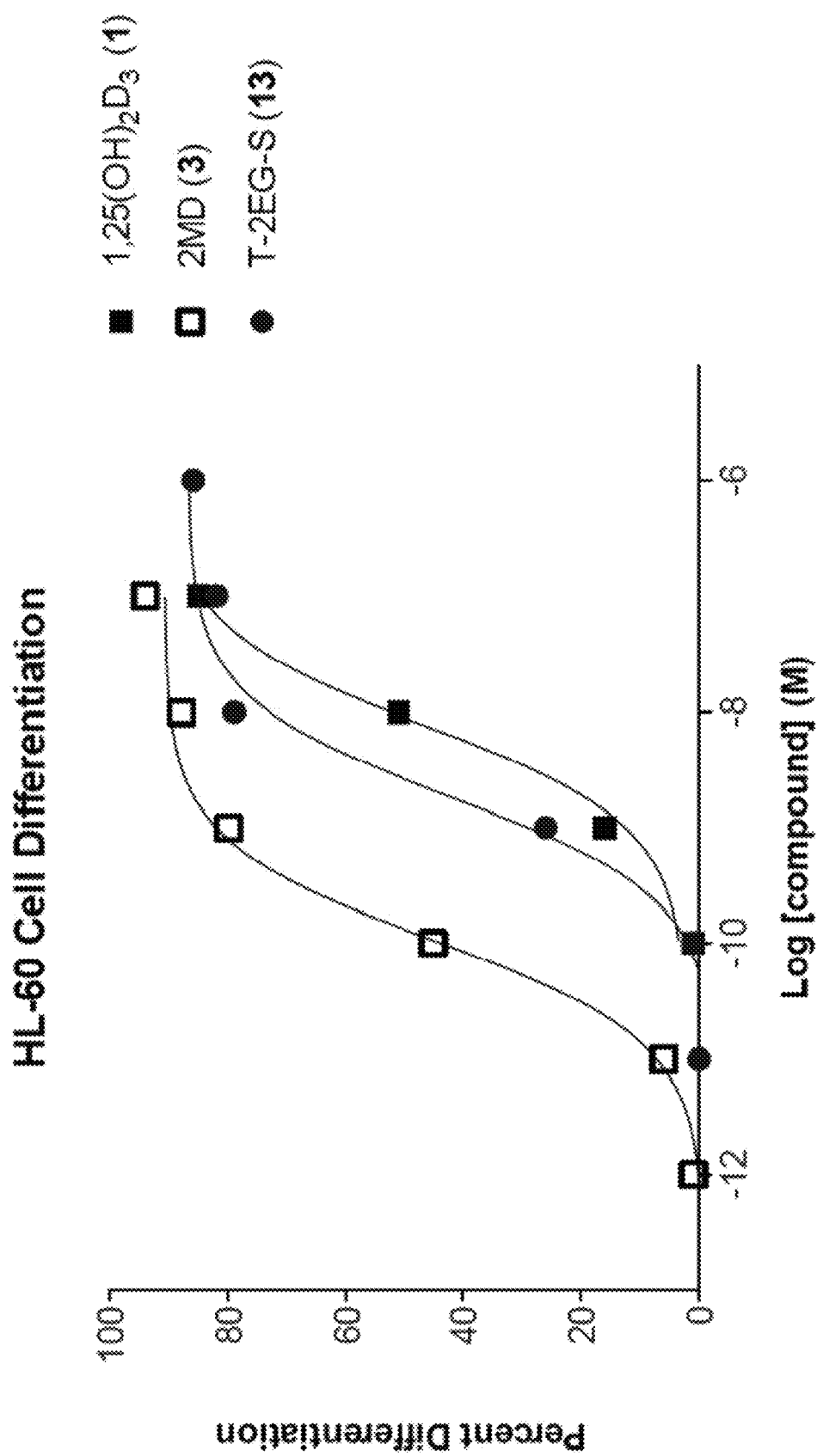
FIG. 11. Differentiation activity of 1α,25-(OH)$_2$D$_3$ (1), 2MD (3) and the synthesized vitamin D analog 13.
Figure 12:
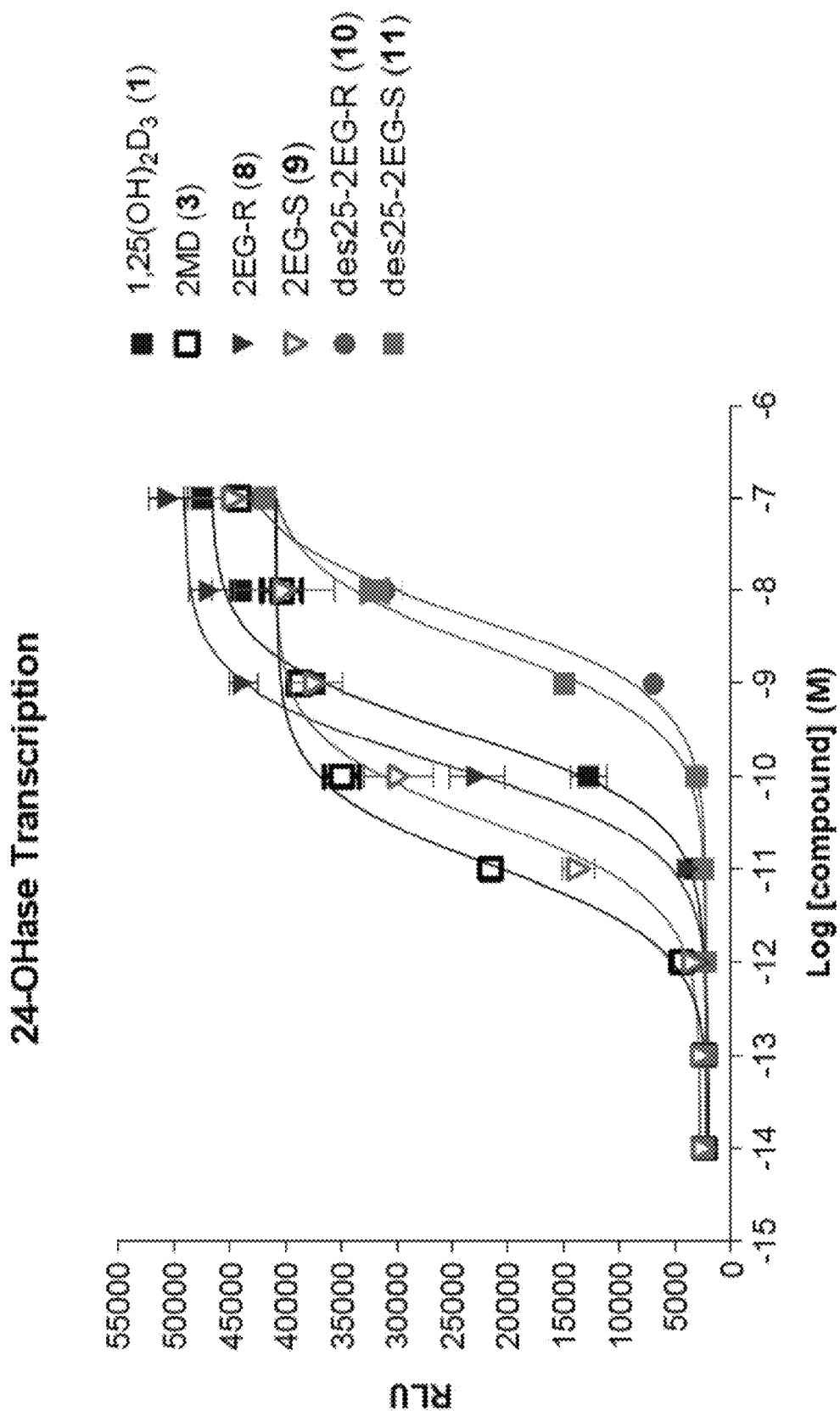
FIG. 12. Transcriptional activity of 1α,25-(OH)$_2$D$_3$ (1), 2MD (3) and the synthesized vitamin D analogs 8-11.
Figure 13:
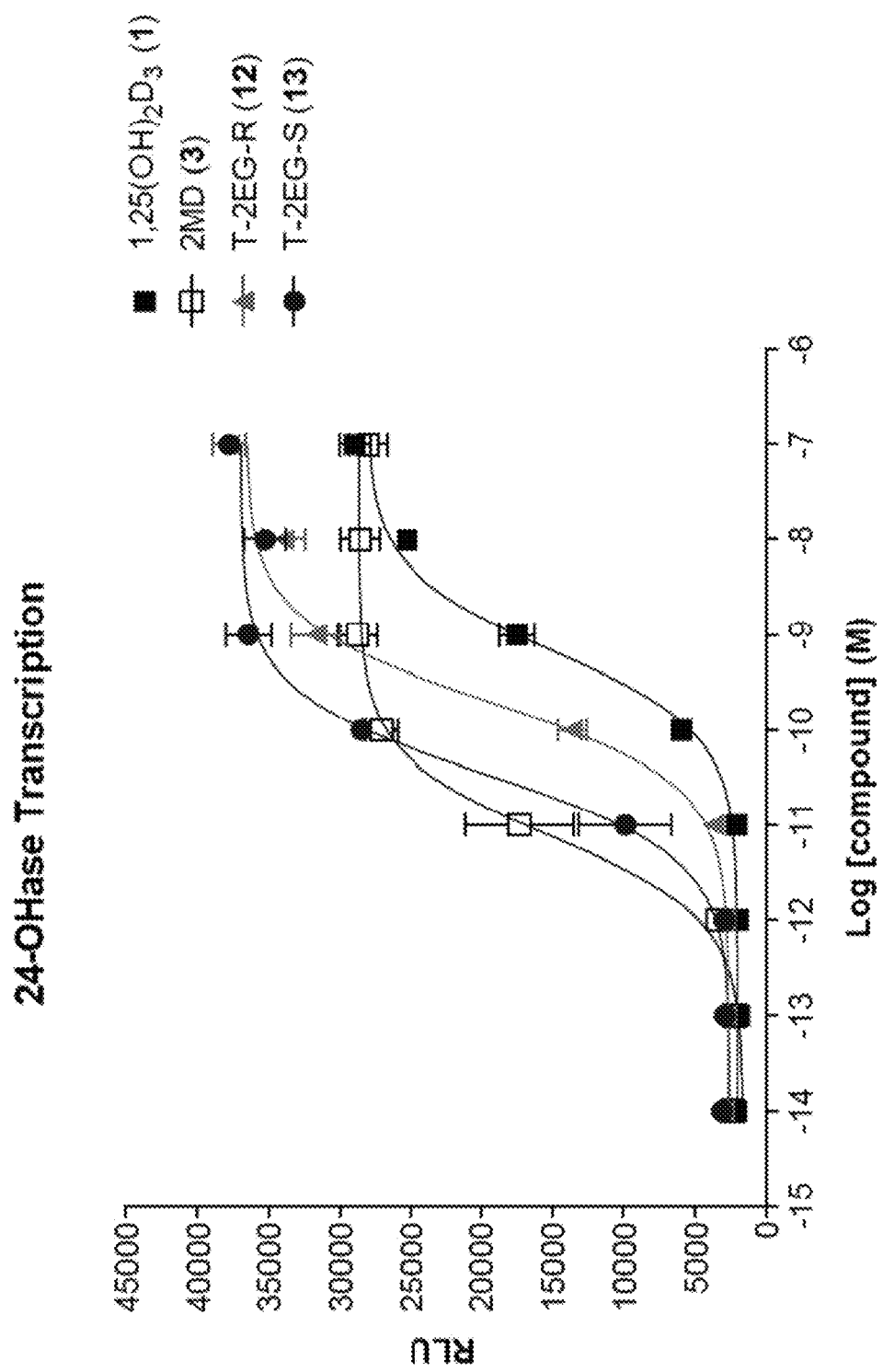
FIG. 13. Transcriptional activity of 1α,25-(OH)$_2$D$_3$ (1), 2MD (3) and the synthesized vitamin D analogs 12 and 13.

The disclosed subject matter further may be described utilizing terms as defined below.

Unless otherwise specified or indicated by context, the terms "a", "an", and "the" mean "one or more." For example, the phrases "a compound" and "an analog" should be interpreted to mean "one or more compounds" and "one or more analogs," respectively.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus ≥10% of the particular term.

As used herein, the terms "include" and "including" have the same meaning as the terms "comprise" and "comprising." The transitional term "comprising" should be interpreted as being "open-ended" such that a claim utilizing the term "comprising" should be interpreted as requiring the recited components but being permitted to include other additional components. The transitional term "consisting essentially of" should be interpreted as being "partially closed" such that a claim utilizing the term "consisting essentially of" should be interpreted as requiring the recited components and permitting only other additional components that do not materially affect the basic and novel characteristics of the claimed subject matter. The transitional term "consisting" should be interpreted as being "closed" such that a claim utilizing the term "consisting" should be interpreted as requiring the recited components and permitting no other additional components.

As used herein, the terms "calcitriol", "1α,25(OH)$_2$D$_3$," and "native hormone" may be used interchangeably.

As used herein, the compound "2EG-R" refers to (20R)-1α,25-dihydroxy-2-methylene-vitamin D$_3$.

As used herein, the compound "2EG-S" refers to (20S)-1α,25-dihydroxy-2-methylene-vitamin D$_3$.

As used herein, the compound "Des25-2EG-R" refers to 1α-hydroxy-2-methylene-vitamin D$_3$.

As used herein, the compound "Des25-2EG-S" refers to (20S)-1α-hydroxy-2-methylene-vitamin D$_3$.

As used herein, the compound "T-2EG-R" refers to the compound (5E,20R)-1α,25-dihydroxy-2-methylene-vitamin D$_3$.

As used herein, the compound "T-2EG-S" refers to the compound (5E,20S)-1α,25-dihydroxy-2-methylene-vitamin D$_3$.

As used herein, the compound "2MD" refers to (20S)-1α,25-dihydroxy-2-methylene-19-nor vitamin D$_3$. (See DeLuca et al., U.S. Pat. No. 5,843,928).

The compounds (20R)-1α,25-dihydroxy-2-methylene-vitamin D$_3$, (20S)-1α,25-dihydroxy-2-methylene-vitamin D$_3$, and (5E,20S)-1α,25-dihydroxy-2-methylene-vitamin D$_3$ and synthesis methods therefor have been disclosed. (See U.S. Pat. No. 8,410,080, the content of which is incorporated herein by reference in its entirety).

The presently disclosed analogs are characterized by the general formula I or II or by the specific formula Ia, Ib, Ic, Id, IIa, or IIb. The pro-drug form and protected-hydroxy form of the presently disclosed analogs also are characterized by general formula I or II (e.g., where $X_1$ and $X_2$ are hydroxy-protecting groups as disclosed herein and as known in the art. As contemplated herein, a "protected hydroxy" group is a hydroxy group derivatized or protected by any of the above groups commonly used for the temporary or permanent protection of hydroxy functions (e.g., a silyl, alkoxyalkyl, acyl or alkoxycarbonyl groups, as described herein). A "hydroxy-protecting group" signifies any group commonly used for the temporary protection of hydroxy functions, such as for example, alkoxycarbonyl, acyl, alkyl-silyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl. Other protecting groups include benzyloxycarbonyl or allyloxycarbonyl protecting groups. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. As contemplated herein, the word "alkyl" as used in the description or the claims, denotes a straight-chain or branched alkyl radical of 1 to 6, 7, 8, or 9, 10 carbons, in all its isomeric forms. "Alkoxy" refers to any alkyl radical which is attached by oxygen (i.e., a group represented by "alkyl-O—"). Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group. The terms "hydroxyalkyl", "deuteroalkyl" and "fluoroalkyl" refer to an alkyl radical substituted by one or more hydroxy, deuterium, or fluoro groups respectively. An "alkylidene" refers to a radical having the general formula $C_kH_{2k}$— where K is an integer (e.g., where K is 1, 2, 3, 4, 5, 6, 7, 8, 9, or 10).

The preparation of 2-methylene vitamin D$_3$ analogs and related compounds having the general structure I or II or the specific structure Ia, Ib, Ic, Id, IIa, or IIb may be accomplished by methods illustrated in the Examples below in Schemes 1, 2, and 3. Scheme 1 illustrates a method for preparing precursor dienyne 14 which then may be condensed with vinyl triflates 15, 16, 17, or 18 to prepare compounds 8, 9, 10, or 11, and optionally isomerized to prepared compounds 12 and 13. In Schemes 1 and 2 protection of the hydroxy groups is provided by t-butyldimethylsilyl group (TBS). Although TBS groups are utilized in Schemes 1 and 2 as hydroxy-protecting groups, any hydroxy-protecting group, as described herein, may be utilized during the reaction steps.

As disclosed herein, the 2-methylene vitamin D$_3$ analogs and related compounds may be utilized to treat and/or prevent diseases or disorders in patients in need thereof. The terms "patient," "subject," and "individual" may be used interchangeably herein.

A patient in need thereof may include any animal. The animal may be a human, a domestic animal such as a dog, cat, or horse, or an agricultural animal.

A patient in need thereof may refer to patient having or at risk for acquiring a disease or disorders associated with vitamin D activity. For example, a patient in need thereof may include a patient having or at risk for acquiring bone diseases and disorders, which may include, metabolic bone diseases and disorders where an increase in bone mass is desirable such as osteoporosis (e.g., senile osteoporosis, postmenopausal osteoporosis, steroid-induced osteoporosis, and low bone-turnover osteoporosis), osteopenia, and osteomalacia. A patient in need thereof may also include a patient in need of an increase in bone strength.

A patient in need thereof may include a patient having or at risk for developing skin diseases, disorders, and conditions. These may include, but are not limited to psoriasis, acne, lack of adequate skin firmness, lack of adequate dermal hydration, and insufficient sebum secretion.

A patient in need thereof may include a patient having or at risk for developing cell proliferative diseases or disorders such as cancer. These may include, but are not limited to leukemia, colon cancer, breast cancer, skin cancer, and prostate cancer.

A patient in need thereof may include a patient having or at risk for developing autoimmune diseases and disorders. These may include, but are not limited to multiple sclerosis, diabetes mellitus, lupus, host versus graft reaction, and rejection of transplants.

A patient in need thereof may include a patient having or at risk for developing an inflammatory disease or disorder. These may include, but are not limited to rheumatoid arthritis, asthmas, and inflammatory bowel diseases. A patient in need thereof may include having or at risk for developing Crohn's disease and ulcerative colitis.

A patient in need thereof may include a patient having or at risk for developing obesity. A patient in need thereof may include a patient in need of or desirous of inhibiting adipocyte differentiation, inhibiting SCD-1 gene transcription, and/or reducing body fat.

A patient in need thereof may include a patient having or at risk for developing secondary hyperparathyroidism. In particular, a patient in need thereof may include a patient having or at risk for developing secondary hyperparathyroidism of renal osteodystrophy.

For prevention and/or treatment purposes, the compounds of this invention defined by general formula I or II or by the specific formula Ia, Ib, Ic, Id, IIa, or IIb may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds of the general formula I or II or the specific formula Ia, Ib, Ic, Id, IIa, or IIb may be administered orally, topically, parenterally, rectally, nasally, sublingually or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications.

A dose of from 0.01 µg to 1000 µg per day of the compounds I or II or of the compounds Ia, Ib, Ic, Id, IIa, or IIb, or from about 20 ng/day to about 1 µg/day, or from about 40 ng/day to about 600 ng/day, or from about 50 ng to about 600 ng per day or from about 100 ng/day to about 400 ng/day may be appropriate for prevention and/or treatment purposes, such dose being adjusted according to the disease to be treated, its severity and the response of the subject as is well understood in the art. Because the compound exhibits specificity of action, each may be suitably administered alone, or together with graded doses of another active vitamin D compound (e.g., 1α-hydroxyvitamin $D_2$ or $D_3$, or 1α,25-dihydroxyvitamin $D_3$) in situations where different degrees of bone mineral mobilization and calcium transport stimulation is found to be advantageous.

Compositions for use in the above-mentioned treatments comprise an effective amount of the formula I or II or of the formula Ia, Ib, Ic, Id, IIa, or IIb, as the active ingredient, and a suitable carrier. An effective amount of such compound for use in accordance with this invention is from about 0.01 µg to about 1000 µg per gm of composition, preferably from about 0.1 µg to about 500 µg per gram of composition, and may be administered topically, transdermally, orally, rectally, nasally, sublingually, or parenterally in dosages of from about 0.01 µg/day to about 1000 µg/day, and preferably from about 0.1 µg/day to about 500 µg/day.

The compounds of the formula I or II or the formula Ia, Ib, Ic, Id, IIa, or IIb, may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds of the formula I or II or of the formula Ia, Ib, Ic, Id, IIa, or IIb, may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100µ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

EXAMPLES

The following Examples are illustrative and are not intended to limit the scope of the claimed subject matter.

Synthesis and Biological Activity of 2-Methylene Analogs of Calcitriol and Related Compounds Reference is made to the manuscript entitled "Synthesis and Biological Activity of 2-Methylene Analogues of Calcitriol and Related Compounds," Izabela K. Sibilska, Rafal R. Sicinski, Lori A. Plum, Hector F. DeLuca, *J. Med. Chem.* 2015 Dec. 24; 58(24):9653-62, the content of which is incorporated in this patent application by reference in its entirety.

ABSTRACT

In a search for superagonistic vitamin D analogues, a series of highly calcemic (20R)- and (20S)-isomers of 1α-hydroxy-2-methylene-vitamin $D_3$ and 1α,25-dihydroxy-2-methylene-vitamin $D_3$ have been synthesized. To prepare the desired A-ring dienyne fragment new synthetic approach was applied, starting from the (−)-quinic acid. The obtained building block was then subsequently coupled with the C,D-ring enol triflates, derived from the corresponding Grundmann ketones, using the Sonogashira's reaction. Moreover, (20R)- and (20S)-11α,25-dihydroxy-2-methylene-vitamin $D_3$ compounds with (5E)-configuration were prepared by iodine catalyzed isomerization. All four 2-methylene analogues of the native hormone were characterized by high in vitro activity whereas 25-desoxy vitamins are less potent. Among the synthesized compounds, two of them, 2-methylene calcitriol and its epimer at C-20, were found to be almost as active as 2MD in the bone, but more active in intestine.

INTRODUCTION

The most active metabolite of vitamin $D_3$, 1α,25-dihydroxyvitamin $D_3$ [calcitriol, 1α,25-$(OH)_2D_3$, 1, FIG. 1), commonly considered as its hormonal form, plays a crucial role in calcium and phosphate homeostasis.[1] In addition, the continued studies have proved that the physiological role of calcitriol in living organisms is much broader than previously thought and includes also regulation of such processes as cellular growth, cell differentiation, antiproliferation, apoptosis as well as immunomodulation.[2] Although these findings stimulated search for less calcemic calcitriol analogues with potential application as, for example, anticancer agents, highly calcemic agonists have also attracted considerable interest.[3]

In 1998 it was discovered[4] that a "shift" of an exomethylene substituent in the calcitriol molecule from C-10 to C-2, resulting in compound 2 with two A-ring allylic hydroxyls, significantly increased calcemic potency of the analogue. This effect was even more pronounced in the compound with the unnatural 20S-configuration: the analogue 3 (2MD) turned out to strongly stimulate bone formation in vitro[5] as well as in the ovariectomized (OVX) rat model.[6] Moreover, in the recent clinical trial compound 3 proved its ability to increase bone turnover in postmenopausal woman.[7] These findings stimulated synthesis of several other 2-methylene-19-norvitamin D analogues acting as possible agents for the treatment of osteoporosis.[8] Considering a unique role of the 2-methylene group as a structural unit strongly influencing the biological activity of vitamin D compounds, 1-desoxy[9] and 3-desoxy analog of 2MD[10] also were synthesized. In addition, the preparation of (20R)- and (20S)-25-hydroxy-2-methylene-vitamin $D_3$ compounds 4 and 5,[11] and very recently 3-desoxy-1α,25-dihydroxy-2-methylene-vitamin $D_3$ (6 and 7) isomeric at C-20 have also been described.[12] Biological activities of these analogues were compared with previously obtained 2-methylene-substituted vitamin D compounds. All four vitamins 4-7, possessing both exomethylene moieties at C-2 and C-10, were characterized by pronounced in vivo calcemic activity. However, the lack of 3β- and, especially, 1α-hydroxyl groups in their structures resulted in considerable diminished VDR binding affinity of analogues. Since it has also been proved that enzymatic 1α-hydroxylation of 2,10-dimethylene compounds 4 and 5 was much slower in comparison with 25-hydroxyvitamin $D_3$, the present inventors focused on compounds having in ring A both hydroxyls (1α and 3β) and two exomethylene substituents located at C-2 and C-10.[13] In the present Example, the inventors describe the synthesis of 2-methylene analogues of (20R)- and (20S)-1α,25-$(OH)_2D_3$ (8 and 9, respectively), their isomers in 5E-series (12 and 13) and the corresponding 25-desoxy counterparts (10 and 11).

Results and Discussion

Chemistry

Considering the fact that the bicyclic vinyl triflates 15-17 were known compounds, and also 18 could be easily prepared from the respective Grundmann ketone by the same method, the present inventors concentrated their efforts on the synthesis of the required A-ring dienyne building block 14. New synthetic route has been elaborated, starting from the commercially available (−)-(1S,3R,4S,5R)-quinic acid (19).

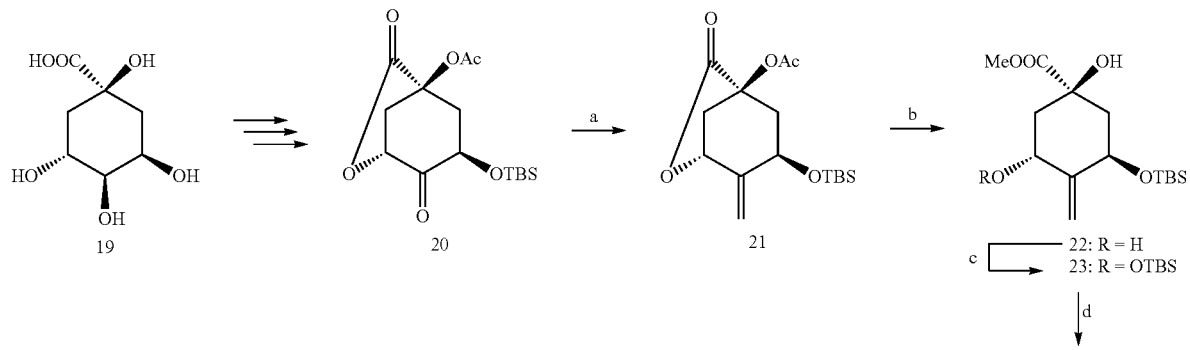

Scheme 1.

-continued

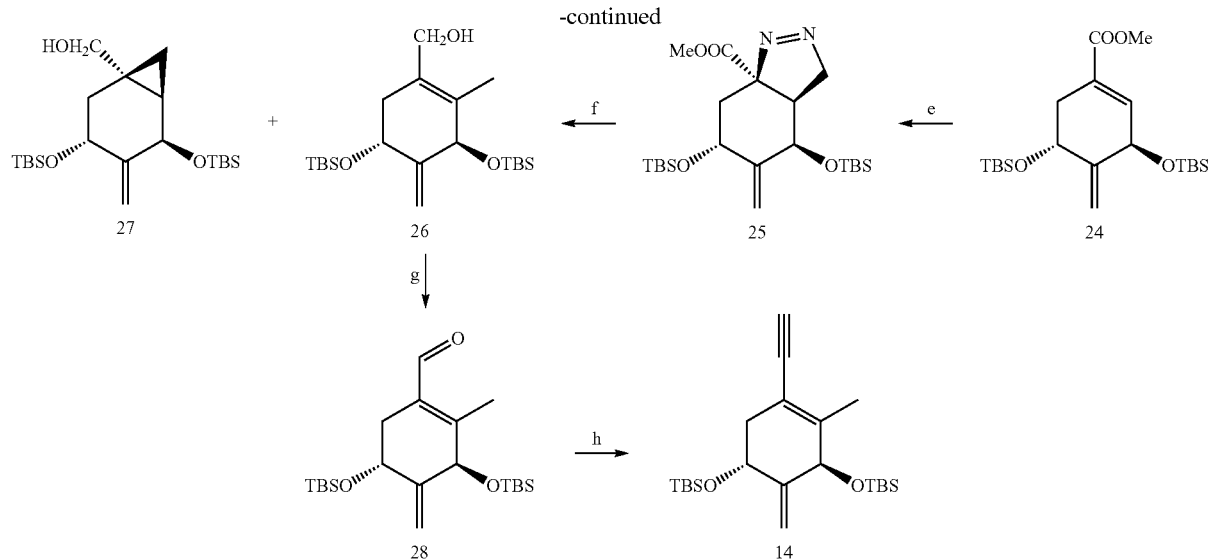

(a) Ph$_3$P$^+$CH$_3$Br$^-$, t-BuOK, THF, 73%; (b) CH$_3$OMe, MeOH, 79%; (c) TBSOTf, 2,6-lutidine, CH$_2$Cl$_2$, 95%; (d) Martin sulfurane, CCl$_4$, 90%; (e) CH$_2$N$_2$, Et$_2$O, 99%; (f) i. DMF, 125° C.; ii. DIBALH, CH$_2$Cl$_2$/toluene, chrom. separation (26: 60% and 27: 34%; two steps); (g) PDC, CH$_2$Cl$_2$, 79%; (h) n-BuLi, TMSCHN$_2$, THF, 82%.

A synthetic route to the A-ring fragment 14 construction started from the keto lactone 20 (Scheme 1) prepared from the quinic acid 19 by the described method.[14] Wittig reaction introduced the exomethylene substituent at the early stage of the synthesis and the following methanolysis of the lactone moiety in 21 gave the dihydroxy ester 22. After hydroxyl protection, compound 23 was obtained and, as a result of the symmetrical substitution of its cyclohexane ring, the subsequent dehydration process with Martin sulfurane furnished a single elimination product 24. Introduction of the methyl group into β-position of this unsaturated ester was achieved by the method described by Desmaele and Tanier.[15] Treatment of 24 with diazomethane solution resulted in formation of bicyclic adduct 25 as a product of 1,3-dipolar cycloaddition. Taking into account the literature data,[16] the observed regioselectivity of the reaction was expected, however high stereoselectivity of this process was somewhat surprising. Apparently, cycloaddition of diazomethane occurred solely from the side of an allylic OTBS substituent. Inspection of the $^1$H NMR spectra of the formed adduct 25, supported by molecular mechanics calculations, allowed us to establish its structure. The subsequent thermolysis process of 25 followed by DIBALH reduction provided two isomeric compounds. Advantageously, the yield of the desired allylic alcohol 26, a direct precursor of the A-ring fragment 14, was significantly higher (60%) than that of the minor bicyclic product 27 (34%). Oxidation of the formed allylic alcohol 26 with PDC afforded the aldehyde 28 that reacted with the anion of trimethylsilyldiazomethane leading to the target dienyne 14.

The A-ring building block 14 was than coupled with the C,D-ring vinyl triflates 15-18, obtained from the corresponding Grundmann ketones.[17] Three former hydrindane compounds were described in literature[12,18,19] and the last one (18) was prepared by us on the analogous way. Thus, Sonogashira reaction of dienyne 14 with the vinyl triflate 15 carried out using reaction conditions described by Mourino[21] furnished the expected trienyne 29 (Scheme 2) in which triple bond was then selectively hydrogenated in a presence of Lindlar catalyst poisoned with quinoline.

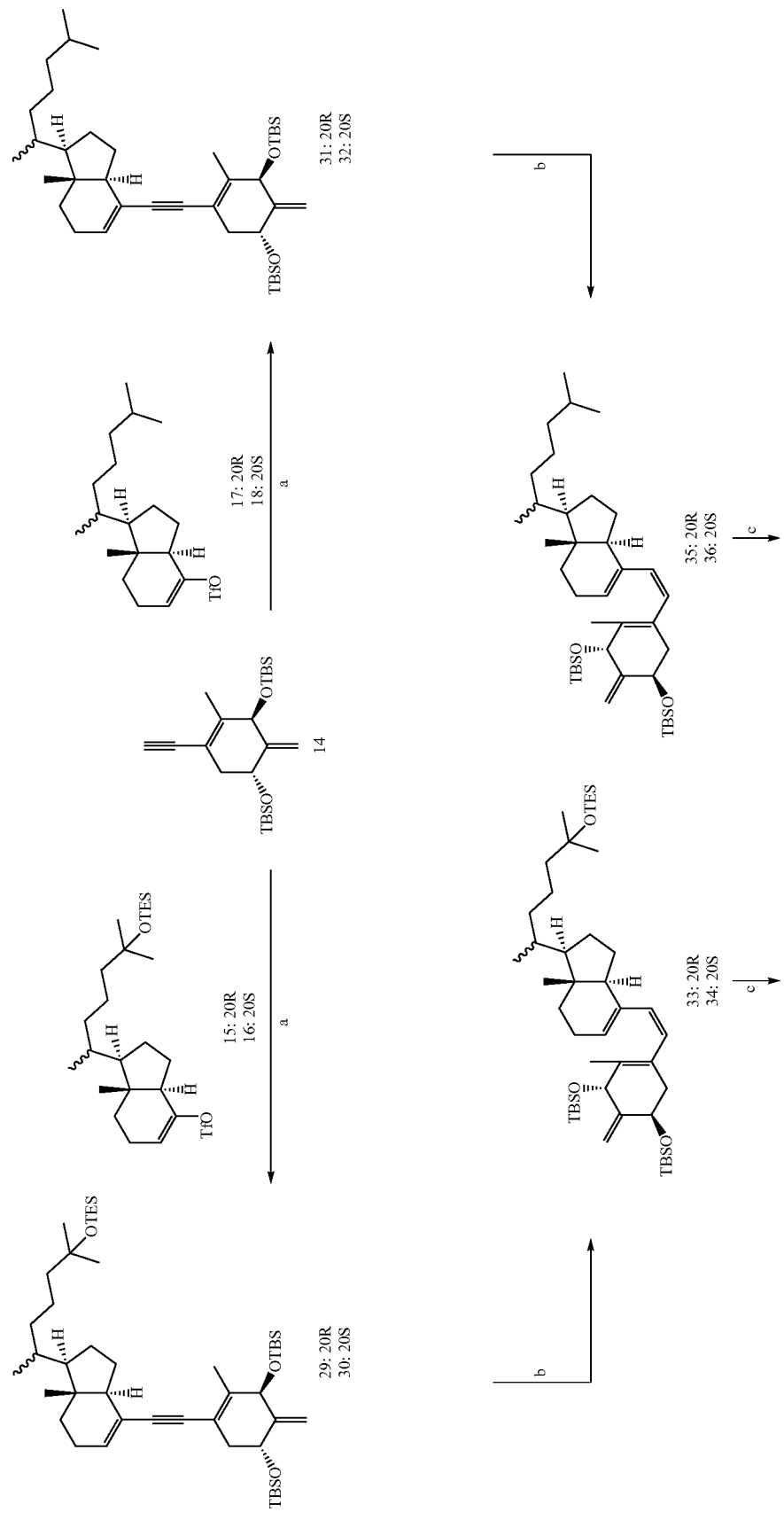

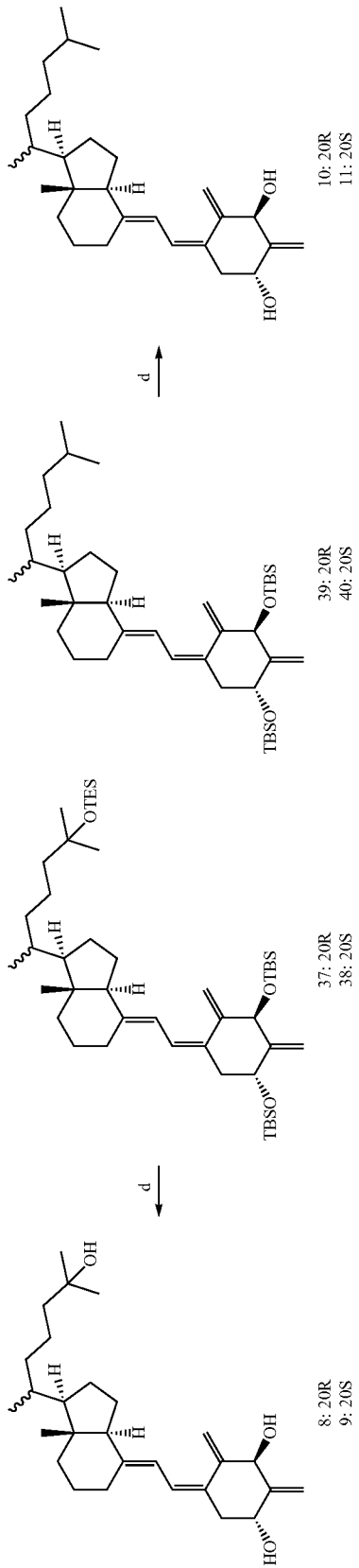

Thermal rearrangement of the obtained previtamin D analogue 33 afforded the protected vitamin D compound 37 in quantitative yield. Removal of the three silyl protecting groups was less efficient but provided the target 2-methylene-1α,25-(OH)$_2$D$_3$ (8). The Sonogashira protocol was also applied for other coupling reactions between dienyne 14 and the vinyl triflates 16-18 and the obtained trienynes 30-32 were converted to the respective final vitamin D analogues 9-11 as it was described above. For the preparation of the 5E-compounds 12 and 13, the well-known iodine-catalyzed isomerization[20] was applied (Scheme 3).

Scheme 3.

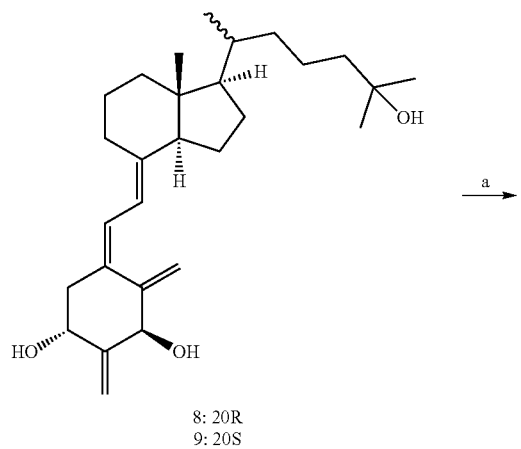

8: 20R
9: 20S a →

-continued

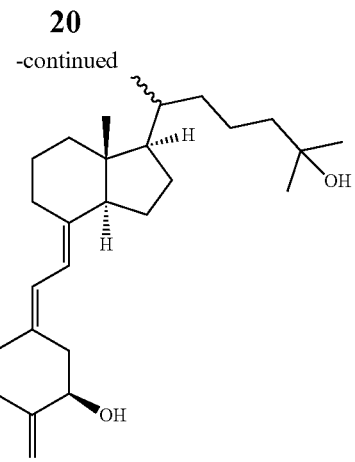

12: 20R
13: 20S (a) I$_2$, hv, Et$_2$O (12: 65%, 13: 64%)

Biological Evaluation.

Biological activity of all the synthesized 2-methylene-vitamin D compounds was examined using both in vitro and in vivo tests. In the first competitive binding assay, the affinity of vitamins to the full-length recombinant rat receptor was evaluated and compared to 1α,25-(OH)$_2$D$_3$ (1) and 2MD (3). It was established (Table 1) that 2-methylene substituted calcitriol 8, as well as its (20S)- and (5E,20S)-isomers bound the VDR almost as effectively as the natural hormone 1, whereas (5E)-compound 12 had 2.5-fold higher affinity to the receptor. The lack of 25-hydroxyl in the analogues 10 and 11 resulted in their significantly lower binding ability, decreased by two orders of magnitude in comparison with 1.

TABLE 1

Relative VDR Binding Activities, [a]HL-60 Differentiating Activities, [b]and Transcriptional Activities[c] of the Vitamin D Hormone (2), 2MD (3) and the Vitamin D Analogues 8-13.

| Compd. Structure | Comp. No. | VDR Binding[a] K$_i$ Ratio | HL-60[b] differentiation ED$_{50}$ Ratio | 24OHase[c] transcription ED$_{50}$ Ratio |
|---|---|---|---|---|
| 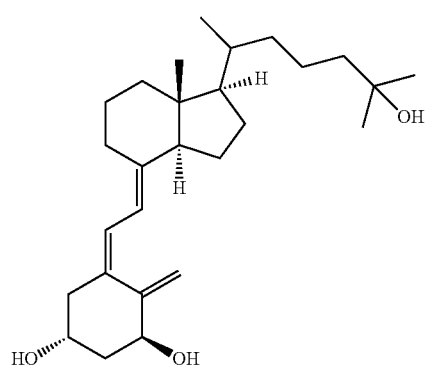 [SMILES: C=C1/C(=C\C=C2/CCC[C@]3(C)[C@@H](C(C)CCCC(C)(C)O)CC[C@@H]23)C[C@@H](O)C[C@@H]1O] | 2 | 1 | 1 | 1 |

TABLE 1-continued

Relative VDR Binding Activities,[a] HL-60 Differentiating Activities,[b] and Transcriptional Activities[c] of the Vitamin D Hormone (2), 2MD (3) and the Vitamin D Analogues 8-13.

| Compd. Structure | Comp. No. | VDR Binding[a] $K_i$ Ratio | HL-60[b] differentiation $ED_{50}$ Ratio | 24OHase[c] transcription $ED_{50}$ Ratio |
|---|---|---|---|---|
| | 3 | 1 | 25 | 29 |
| | 8 | 1.4 | 0.7 | 1 |
| | 9 | 1.1 | 29 | 10 |
| | 10 | 0.01 | 0.07 | 0.07 |
| | 11 | 0.01 | 0.7 | 0.07 |

TABLE 1-continued

Relative VDR Binding Activities,[a] HL-60 Differentiating Activities,[b] and Transcriptional Activities[c] of the Vitamin D Hormone (2), 2MD (3) and the Vitamin D Analogues 8-13.

| Compd. Structure | Comp. No. | VDR Binding[a] $K_i$ Ratio | HL-60[b] differentiation $ED_{50}$ Ratio | 24OHase[c] transcription $ED_{50}$ Ratio |
|---|---|---|---|---|
| | 12 | 2.5 | 0.4 | 1 |
| | 13 | 1.1 | 20 | 5 |

[a] Competitive binding of 1α,25-(OH)$_2$D$_3$ (1) and the synthesized vitamin D analogues to the full-length recombinant rat vitamin D receptor. The experiments were carried out in duplicate on two different occasions.

The $K_i$ values are derived from the dose-response curves and represent the inhibition constant when radiolabeled 1α,25-(OH)$_2$D$_3$ is present at 1 nM and a $K_d$ of 0.2 nM is used. The numbers shown in the Table are expressed as the average ratio of the 1α,25-(OH)$_2$D$_3$ $K_i$ to the $K_i$ for the analogue. [b] Induction of differentiation of HL-60 promyelocytes to monocytes by 1α,25-(OH)$_2$D$_3$ (1) and the synthesized vitamin D analogues. Differentiation state was determined by measuring the percentage of cells reducing nitro blue tetrazolium (NBT). The experiment was repeated in duplicate two times. The $ED_{50}$ values are derived from the dose-response curves and represent the analogue concentration capable of inducing 50% maturation. The numbers shown in the Table are expressed as the average ratio of the 1α,25-(OH)$_2$D$_3$ $ED_{50}$ to the $ED_{50}$ for the analogue. [c] Transcriptional assay in rat osteosarcoma cells stably transfected with a 24-hydroxylase gene reporter plasmid. The $ED_{50}$ values are derived from dose-response curves and represent the analogue concentration capable of increasing the luciferase activity by 50%. The numbers shown in the Table are expressed as the average ratio of the 1α,25-(OH)$_2$D$_3$ $ED_{50}$ to the $ED_{50}$ for the analogue.

The next assay confirmed that, with an exception of 10, the obtained compounds exerted also pronounced antiproliferative effects. Thus, the highest ability to elicit cellular differentiation of human promyelocytic HL-60 cells into monocytes, exceeding or approaching that of 2MD, was established for (20S)-compounds, the analogue 9 and its (5E)-counterpart 13, respectively.

The activity of the synthesized vitamins in inducing transcription of vitamin D target gene was examined using the 24-hydroxylase (CYP-24) promoter. Both analogues 8 and 12, with the natural configuration at C-20, exhibited the same transcriptional potency as 1α,25-(OH)$_2$D$_3$ (1). 25-Desoxy-compounds 10 and 11 also induced a dose-dependent activation of the CYP24A1 gene but decreased by one order of magnitude as compared with 1. As in the previous assay, of all tested vitamins, the most pronounced activity was exhibited by (20S)-analogues 9 and 13.

The results of in vivo testing of the analogues described in this Example clearly indicated that 2-methylene calcitriol (8) and its isomer 9 with an "unnatural" (20S)-configuration displayed the highest potency in raising serum calcium in rats. Their 25-desoxy counterparts 10 and 11 were less active but still more calcemic than calcitriol. Interestingly, the (5E)-configuration was not beneficial, because both analogues 12 and 13, had significantly decreased activity in bone. The same pattern of activity was observed when intestinal calcium activity of the vitamins was tested. Much higher potency on intestine of compounds 8 and 9 as compared to calcitriol indicates that these superagonistic vitamins are significantly more active in this assay than 2MD (it was shown that 3 had ca. 30 times higher activity in the bone tissue than 1 whereas activity of both compounds in the intestine was similar).[4,5]

CONCLUSION

Here, the inventors report a continuation of structure-activity studies on the vitamin D analogues with 2-methylene substituents. New synthetic paths were used, providing the desired target vitamins which were subjected to biological testing. Introduction of an additional A-ring exomethylene group at C-2 in 1α,25-(OH)$_2$D$_3$ (1) led to 2-methylene calcitriol (8) characterized by very similar biological activity in vitro but considerably higher potency in both in vivo assays, bone calcium mobilization and intestinal calcium transport. Trying to evaluate an effect of exomethylene substituents by comparison to the biological activities of 3 and its analogues 9 and 13 it can be pointed out that all these compounds have almost identical VDR binding ability and HL-60 differentiating potency, however, transcriptional activity of the 2MD analogues with an additional 10-methylene (compound 9) or pseudo-4-methylene group (compound 13) was decreased three and six times, respectively. In vivo activity of (20S)-2-methylene-1α,25-(OH)$_2$D$_3$ (9) in the bone tissues was found to be slightly lower than that of 3, similar to its 20R-epimer 8 and ca. one order of magnitude higher compared to calcitriol. However, in the intestine both compounds 8 and 9 proved to be more potent than 1 and 3.

Strong calcemic activity of 25-analogues 10 and 11 lacking 25-hydroxyl indicated their efficient enzymatic hydroxylation in the living organism. Therefore, these compounds can be considered as potential prodrugs.

EXPERIMENTAL SECTION

Chemistry

Optical rotations were measured in chloroform using a Perkin-Elmer models 241 and 343 polarimeter at 22° C. Ultraviolet (UV) absorption spectra were obtained on a Shimadzu UV-1800 UV spectrophotometer in 100% EtOH. All nuclear magnetic resonance spectra were recorded in deuteriochloroform using Varian Unity plus (200 MHz), Bruker DMX-400 (400 MHz), Bruker DMX-500 (500 MHz). COSY spectra, spin decoupling as well as NOE, DEPT 90 and DEPT 135 experiments were used to assign particular signals in the 1H and $^{13}$C NMR spectra. Chemical shifts (δ) are reported in parts per million relative to $CH_3Si$ (δ 0.00) as an internal standard. Abbreviations used are singlet (s), doublet (d), triplet (t), quartet (q), multiplet (m). High resolution mass spectra were registered on LCT (TOF) or Mass Quattro LC spectrometers. High-performance liquid chromatography (HPLC) was performed on a Waters Associates liquid chromatograph equipped with a model 6000A solvent delivery system, model U6K Universal injector, and model 486 tunable absorbance detectors. Solvents were dried and distilled following standard procedures.

The purity of final compounds was determined by HPLC, and they were judged at least 99% pure. Two HPLC columns (9.4 mm×25 cm Zorbax-Sil and 9.4 mm×25 cm Zorbax Eclipse XDB-C18) were used as indicated in Table 2 (Supporting Information). The purity and identity of the synthesized vitamins were additionally confirmed by inspection of their $^1$H NMR and high-resolution mass spectra.

The known vinyl triflates 15,[20] 16,[12] and 17,[21] were obtained according to the procedure of De Clercq et al.,[xxi] analogous method was used for the preparation of the (20S)-trilate 18 from the corresponding Grundmann ketone. The starting lactone 20[18] was synthesized from (−)-quinic acid (19).

(20S)-8-Trifluoromethanesulfonyloxy-des-A,B-cholest-8-ene (18)

A solution of (20S)-des-A,B-cholestan-8-one (121 mg, 458 mol) in anhydrous THF (2 mL) was slowly added to the solution of LDA (2.0 M in THF/heptane/ethylbenzene; 255 μL, 510 μmol) in dry THF (0.6 mL) at −78° C. under argon. Then a solution of N-phenyltriflimide (185 mg, 518 μmol) in dry THF (1 mL) was added. After 1 h a cooling bath was removed and the reaction mixture was allowed to warm up to room temperature. Stirring was continued for 30 min and water was added. The mixture was extracted with hexane, dried ($MgSO_4$) and concentrated. The residue was applied on a silica Sep-Pak cartridge and eluted with hexane to afford the enol triflate 18 (123 mg, 85% considering recovered substrate) and unreacted ketone (25 mg).

(1R,3R,5R)-1-Acetoxy-3-[(tert-butyldimethylsilyl)oxy]-4-methylene-6-oxabicyclo [3.2.1]octan-7-one (21)

A solution of potassium tert-butoxide in THF (1.0 M; 746 μL, 746 μmol) was added dropwise to a stirred suspension of methyl triphenylphosphonium bromide (280 mg, 784.6 μmol) in anhydrous THF (5.5 mL) at 0° C. The mixture was warmed up to room temperature and stirred for additional 10 min. A solution of lactone 20 (126 mg, 382.7 μmol) in THF (1.6 mL) was added via cannula and stirring was continued at room temperature for 1 h. Water was added and the mixture was extracted with ethyl acetate, dried ($MgSO_4$) and concentrated. The residue was applied on a silica Sep-Pak cartridge (5 g) and eluted with hexane/ethyl acetate (95:5) to afford compound 21 (91 mg, 73%).

(3R,5R)-5-[(tert-butyldimethylsilyl)oxy]-1,3-dihydroxy-4-methylene-cyclohexanecarboxylic acid methyl ester (22)

A solution of compound 21 (330 mg, 1.01 mmol) was vigorously stirred in methanolic sodium methoxide solution (0.04 M; 10 mL, 0.4 mmol) at room temperature for 17 h under argon. Water was added and the mixture was extracted with ethyl acetate, dried ($Na_2SO_4$) and concentrated. The residue was applied on a silica Sep-Pak cartridge (5 g) and eluted with hexane/ethyl acetate (7:3) to give the diol 22 (253 mg, 79%) as a colorless oil.

(3R,5R)-3,5-Bis[(tert-butyldimethylsilyl)oxy]-1-hydroxy-4-methylene-cyclohexanecarboxylic Acid Methyl Ester (23)

2,6-Lutidine (191 μL, 1.65 mmol) was dropwise added to a stirred solution of the diol 22 (274 mg, 865.8 μmol) in anhydrous methylene chloride (4.5 mL) at −40° C. followed by tert-butyldimethylsilyl trifluoromethanesulfonate (300 μL, 1.3 mmol). The stirring was continued at −40° C. for 1 h and saturated $NaHCO_3$ was added. Cooling bath was removed and the reaction mixture was allowed to warm up slowly to room temperature. The mixture was extracted with methylene chloride, and combined organic layers were washed with 5% HCl and water, dried ($Na_2SO_4$) and concentrated. The residue was applied on a silica Sep-Pak cartridge (10 g) and eluted with hexane/ethyl acetate (93:7) to give compound 23 (353.5 mg, 95%) as a colorless oil.

(3R,5R)-3,5-Bis[(tert-butyldimethylsilyl)oxy]-4-methylene-cyclohex-1-enecarboxylic acid methyl ester (24)

To a stirred solution of alcohol 23 (326 mg, 756.8 mol) in anhydrous carbon tetrachloride (8.2 mL) was added a solution of bis[α,α-bis(trifluoromethyl)benzyloxy]diphenylsulfur (752 mg, 1.12 mmol) in anhydrous carbon tetrachloride (6 mL) at room temperature under argon. Reaction was stirred for 30 min, water was added and the mixture was extracted with methylene chloride. The organic phase was dried ($Na_2SO_4$) and concentrated. The resulting residue was applied on a silica Sep-Pak cartridge (5 g) and eluted with hexane/diethyl ether (98:2) to give the desired product contaminated by dehydrating reagent. Further purification on preparative TLC plates (Silica Gel 60$F_{254}$, 20×20 cm, layer thickness 250 nm) using hexane/diethyl ether (92:8) afforded unsaturated ester 24 (276 mg, 90%) as a colorless oil.

(3aR,4R,6R,7aR)-4,6-Bis[(tert-butyldimethylsilyl)oxy]-5-methylene-3,3a,4,5,6,7-hexahydro-indazole-7a-carboxylic acid methyl ester (25)

Solution of diazomethane in diethyl ether [2.7 mL; (prepared according to the procedure of Arndt)][24] was added to a solution of the ester 24 (264 mg, 639.7 mol) in anhydrous ethyl ether (1 mL) at room temperature. Reaction mixture was protected from light and stirred for 2 h. Solvent was evaporated, a residue dissolved in hexane, applied on a silica Sep-Pak cartridge (5 g) and eluted with hexane/ethyl acetate (97:3) to give bicyclic adduct 25 (288 mg, 99%) as colorless oil.

[(3'R,5'R)-3',5'-Bis[(tert-butyldimethylsilyl)oxy]-2'-methyl-4'-methylene-cyclohex-1'-enyl]-methanol (26) and [(1'S,3'R,4'S,'5'R,6'R)-3',5'-Bis-[(tert-butyldimethylsilyl)oxy]-4'-[(trimethylsilyl)oxy]-bicyclo[4.1.0]hept-1-yl]-methanol (27)

A solution of compound 25 (39 mg, 162.8 mol) in freshly distilled anhydrous DMF (1.7 mL) was stirred at 125° C. for 6 h under argon. Heating bath was removed, water was added and the mixture was extracted with hexane, dried ($Na_2SO_4$) and concentrated. The crude product was applied on a silica Sep-Pak cartridge (2 g) and eluted with hexane/diethyl ether (97:3). Removal of the solvents gave an oily residue (25 mg) that was dissolved in toluene/methylene chloride (2:1, 3 mL). To this solution diisobutylaluminum hydride (1.0 M in toluene; 260 μL, 260 mmol) was slowly added at −78° C. under argon and stirred for 2 h. The mixture was quenched by a slow addition of potassium-sodium tartrate (2N, 4 mL), aqueous HCl (2N, 4 mL) and $H_2O$ (16 mL) and extracted with ethyl acetate. The combined organic layers were washed with brine, dried ($MgSO_4$) and concentrated. The residue was applied on a silica Sep-Pak cartridge (2 g) and eluted with hexane/ethyl acetate (98:2) to give the allylic alcohol 26 (14 mg, 60%) and bicyclic product 27 (8 mg, 34%).

(3R,5R)-3,5-Bis[(tert-butyldimethylsilyl)oxy]-2-methyl-4-methylene-cyclohex-1-enecarbaldehyde (28)

The mixture of alcohol 26 (16 mg, 40.2 μmol) and pyridinium dichromate (48.5 mg, 225.1 mol) in anhydrous methylene chloride (0.7 mL) was stirred vigorously at room temperature for 4 h. The reaction mixture was then filtered through a pad of Celite (washed with methylene chloride) and the solvents were removed under reduced pressure. The crude product was applied on a silica Sep-Pak cartridge and eluted with hexane/diethyl ether (98:2) to yield the aldehyde 28 (12.6 mg, 79%) as a colorless oil.

(3R,5R)-3,5-Bis[(tert-butyldimethylsilyl)oxy]-1-ethynyl-2-methyl-4-methylene-cyclohexene (14)

n-Buthyllithium (1.6 M in hexanes; 25.5 μL, 40.8 μmol) was added to a solution of (trimethylsilyl)diazomethane (2.0 M in hexane, 19.5 μL, 39 mol) in anhydrous THF (50 μL) at −78° C. under argon, and a solution of aldehyde 28 (12.6 mg, 31.8 mol) in dry THF (100 μL+50 μL) was added via cannula. After 1 h the cooling bath was removed and stirring was continued at room temperature overnight. Water was added, and the mixture was extracted with hexane, dried ($Na_2SO_4$) and concentrated. The crude product was applied on a silica Sep-Pak cartridge and eluted with hexane to afford dienyne 14 (10 mg, 82%).

1α,3β-Bis[(tert-butyldimethylsilyl)oxy]-2-methylene-25-[(triethylsilyl)oxy]-9,10-secocholesta-5(10),8-dien-6-yne (29)

To a solution of dienyne 14 (8 mg, 20.4 mol) and triflate 15 (8.4 mg, 15.9 mol) in anhydrous DMF (200 μL) were added CuI (0.45 mg, 2.37 mol), $(PPh_3)_2Pd(OAc)_2$ (0.34 mg, 0.45 mol) and $Et_2NH$ (159 μL) at room temperature under argon. After 45 min the mixture turned deep reddish-brown. Water was added and the mixture was extracted with hexane, dried ($MgSO_4$) and concentrated. The residue was applied on a silica Sep-Pak cartridge (2 g) and eluted with hexane to afford trienyne 29 (8.3 mg, 92%) and recovered dienyne 14 (2.2 mg).

(20S)-1α,3β-Bis[(tert-butyldimethylsilyl)oxy]-2-methylene-25-[(triethylsilyl)oxy]-9,10-secocholesta-5(10),8-dien-6-yne (30)

Sonogashira reaction of dienyne 14 and triflate 16, performed according to the procedure described above for the coupling of 14 and 15, gave the trienyne 30 (54%).

1α,3β-Bis[(tert-butyldimethylsilyl)oxy]-2-methylene-9,10-secocholesta-5(10),8-dien-6-yne (31)

Sonogashira reaction of triflate 17 and the dienyne 14, performed analogously as described above for the coupling of 14 and 15, gave trienyne 31 (84%).

(20S)-1α,3β-Bis[(tert-butyldimethylsilyl)oxy]-2-methylene-9,10-secocholesta-5(10),8-dien-6-yne (32)

Sonogashira reaction of the triflate 18 and the dienyne 14 was performed analogously as described above for the coupling of 14 and 15 to afford trienyne 32 (98%).

1α-[(tert-Butyldimethylsilyl)oxy]-2-methylene-25-[(triethylsilyl)oxy]-vitamin $D_3$ tert-butyldimethylsilyl ether (37). To a solution of the trienyne 29 (8.3 mg, 10.8 mol) in hexane (3 mL) and quinoline (2 μL) was added Lindlar catalyst (25 mg) and the mixture was stirred at room temperature under a positive pressure of hydrogen. Lindlar catalyst was added twice during 2.5 h (in 20 mg portions) and then the mixture was applied on a silica Sep-Pak cartridge (2 g) and eluted with hexane/ether (98:2) to give the silylated previtamin 33 (5.8 mg, 70%). The previtamin was then dissolved in anhydrous hexane (3 mL) and stirred at 60° C. for 14 h under argon. Solvent was evaporated and residue was applied on a silica Sep-Pak cartridge (2 g) and eluted with hexane/diethyl ether (99.6:0.4) to give protected vitamin D compound 37 (5.8 mg, 100%).

(20S)-1α-[(tert-Butyldimethylsilyl)oxy]-2-methylene-25-[(triethylsilyl)oxy]-vitamin $D_3$ tert-butyldimethylsilyl ether (38)

Hydrogenation of trienyne 30, performed according to the procedure described above for 29, gave silylated previtamin 34 (84%). Compound 34 was then subjected to the analogously performed thermal isomerization to give protected vitamin 38 (70%).

1α-[(tert-Butyldimethylsilyl)oxy]-2-methylene-vitamin $D_3$ tert-butyldimethylsilyl ether (39)

Hydrogenation of trienyne 31 was performed analogously as described above for 29. The obtained silylated previtamin 35 (83%) was then subjected to the thermal isomerization to give protected vitamin 39 (70%).

(20S)-1α-[(tert-Butyldimethylsilyl)oxy]-2-methylene-vitamin $D_3$ tert-butyldimethylsilyl ether (40)

Hydrogenation of trienyne 32 was performed analogously as described above for 29. The obtained silylated previtamin 36 (85%) was then subjected to the thermal isomerization to afford protected vitamin 40 (91%).

1α,25-dihydroxy-2-methylene-vitamin $D_3$ (8)

To a solution of protected vitamin 37 (5.8 mg, 7.5 mol) in THF (1 mL) was added tetrabutylammonium fluoride (1.0 M in THF; 450 μL, 450 mol) at room temperature under argon. The stirring was continued for 20 h, brine was added and the mixture was extracted with ethyl acetate. The organic extracts were dried ($MgSO_4$) and evaporated. The residue was purified by HPLC (9.4 mm×25 cm Zorbax-Sil column, 4 mL/min) using hexane/2-propanol (9:1) solvent system; compound 8 (1.28 mg, 40%) was collected at $R_V$ 36 mL. Analytical sample of the vitamin was obtained after reversed-phase HPLC (9.4 mm×25 cm Zorbax Eclipse XDB-C18 column, 4 mL/min) using methanol/water (88:12) solvent system ($R_V$ 33 mL).

(20S)-1α,25-dihydroxy-2-methylene-vitamin $D_3$ (9)

Treatment of protected vitamin 38 with TBAF, performed according to the procedure described above for 37, gave a product that was purified by HPLC (9.4 mm×25 cm Zorbax-Sil column, 4 mL/min) using hexane/2-propanol (92:8) solvent system; vitamin 9 (16%) was collected at $R_V$ 36 mL. Analytical sample of the vitamin was obtained after reversed-phase HPLC (9.4 mm×25 cm Zorbax Eclipse XDB-C18 column, 4 mL/min) using methanol/water (88:12) solvent system ($R_V$ 30 mL).

1α-hydroxy-2-methylene-vitamin $D_3$ (10)

Hydroxyl deprotection of silylated vitamin 39, was performed analogously as described above for 37. The obtained product was purified by HPLC (9.4 mm×25 cm Zorbax-Sil column, 4 mL/min) using hexane/2-propanol (95:5) solvent system; vitamin 10 (1.8 mg, 40%) was collected at $R_V$ 34 mL. Analytical sample of the vitamin was obtained after reversed-phase HPLC (9.4 mm×25 cm Zorbax Eclipse XDB-C18 column, 4 mL/min) using methanol/water (97:3) solvent system ($R_V$ 40 mL).

(20S)-1α-hydroxy-2-methylene-vitamin $D_3$ (11)

Hydroxyl deprotection of protected vitamin 40 (11 mg, 17.2 mol) was performed analogously as described above for 37. The product was purified by HPLC (9.4 mm×25 cm Zorbax-Sil column, 4 mL/min) using hexane/2-propanol (95:5) solvent system; vitamin 11 (3.3 mg, 46%) was collected at $R_V$ 34 mL. Analytical sample of the vitamin was obtained after reversed-phase HPLC (9.4 mm×25 cm Zorbax Eclipse XDB-C18 column, 4 mL/min) using methanol/water (97:3) solvent system ($R_V$ 38 mL).

(5E)-1α,25-dihydroxy-2-methylene-vitamin $D_3$ (12)

Treatment of compound 8 in ether with a catalytic amount of iodine (2% of the amount of 8), while keeping the solution under diffuse daylight for 1 h, resulted in its partial isomerization. A mixture of (5Z)- and (5E)-isomers 8 and 12 was formed in a ratio of 3:7, respectively. Compounds were separated by reversed-phase HPLC (9.4 mm×25 cm Zorbax Eclipse XDB-C18 column, 4 mL/min) using methanol/water (84:16) solvent system and analytically pure (5E)-isomer 12 was eluted at $R_V$ 57 mL.

(5E,20S)-1α,25-dihydroxy-2-methylene-vitamin $D_3$ (13)

Analogously, as in the case of 8, iodine-catalyzed isomerization of (5Z)-vitamin 9 to the respective (5E)-isomer 13 was performed. Analytically pure sample of the vitamin 13 was obtained after reversed-phase HPLC (9.4 mm×25 mm Zorbax Eclipse XDB-C18 column, 4 mL/min) using methanol/water (84:16) solvent system ($R_V$ 55 mL).

Biological Studies.

1. In Vitro Studies.

VDR binding, HL-60 differentiation, and 24-hydroxylase transcription assays were performed as previously described.[xxi]

2. In Vivo Studies.

2.1. Bone Calcium Mobilization and Intestinal Calcium Transport.

Male, weanling Sprague-Dawley rats were purchased from Harlan (Indianapolis, Ind.). The animals were group housed and placed on Diet 11 (0.47% Ca)+AEK oil for one week followed by Diet 11 (0.02% Ca)+AEK oil for 3 weeks. The rats were then switched to a diet containing 0.47% Ca[xxiii] for one week followed by two weeks on a diet containing 0.02% Ca. Dose administration began during the last week on 0.02% Ca diet. Four consecutive intraperitoneal doses were given approximately 24 hours apart. Twenty four hours after the last dose, blood was collected from the severed neck and the concentration of serum calcium determined as a measure of bone calcium mobilization. The first 10 cm of the intestine was also collected for the intestinal calcium transport analysis using the everted gut sac method.[25]

All animals were managed in accordance with University of Wisconsin standards and protocols for animal care and use. Our experiments were approved by the College of Agricultural and Life Sciences Institutional Animal Care and Use Committee.

Supplemental Supporting Information

Purity Criteria for the Synthesized Vitamin D Compounds

All vitamin D analogues synthesized by us gave single sharp peaks on HPLC and they were judged at least 99% pure. Two HPLC systems (straight- and reversed-phase) were employed as indicated in the Table 2. The purity and identity of the synthesized vitamins were additionally confirmed by inspection of their $^1H$ NMR and high-resolution mass spectra.

TABLE 2

Purity Criteria for Target Vitamin D Compounds

| Compound | Compd. No. | HPLC Retention Volumes Straight-phase[a] (hexane/2-propanol) | Reversed-phase[b] (methanol/water) |
|---|---|---|---|
| 1α,25-dihydroxy-2-methylene-vitamin $D_3$ | 8 | h/p (92:8) 36 mL | m/w (88:12) 33 mL |
| (20S)-1α,25-dihydroxy-2-methylene-vitamin $D_3$ | 9 | h/p (92:8) 36 mL | m/w (88:12) 30 mL |
| 1α-hydroxy-2-methylene-vitamin $D_3$ | 10 | h/p (95:5) 34 mL | m/w (97:3) 40 mL |
| (20S)-1α-hydroxy-2-methylene-vitamin $D_3$ | 11 | h/p (95:5) 34 mL | m/w (97:3) 38 mL |
| (5E)-1α,25-dihydroxy-2-methylene-vitamin $D_3$ | 12 | h/p (92:8) 36 mL | m/w (84:16) 57 mL |
| (5E,20S)-1α,25-dihydroxy-2-methylene-vitamin $D_3$ | 13 | h/p (92:8) 37 mL | m/w (84:16) 55 mL |

[a]Zorbax-Sil; 9.4 mm × 25 cm column;
[b]Zorbax Eclipse XDB-C18; 9.4 mm × 25 cm column.

Spectral Data of the Synthesized Compounds

(20S)-8-Trifluoromethanesulfonyloxy-des-A,B-cholest-8-ene (18)

$^1$H NMR (500 MHz, $CDCl_3$) δ 0.759 (3H, s, 18-$H_3$), 0.847 (3H, d, J=6.6 Hz, 21-$H_3$), 0.870 (6H, d, J=6.6 Hz, 26- and 27-$H_3$), 1.775 (1H, m), 1.97 (2H, m), 2.29 (2H, m), 2.48 (1H, m), 5.56 (1H, dd, J=7.0, 3.6 Hz, 9-H); $^{13}$C NMR (125 MHz, $CDCl_3$) δ 11.49, 18.55, 21.34, 22.61, 22.70, 23.72, 23.88, 28.05, 28.24, 34.78, 35.47, 35.49, 39.35, 45.20, 50.15, 53.85, 114.05, 149.95; HRMS (ESI) exact mass calculated for $C_{19}H_{31}F_3O_3SNa$ ($M^++Na$) 419.1844. found 419.1845.

(1R,3R,5R)-1-Acetoxy-3-[(tert-butyldimethylsilyl)oxy]-4-methylene-6-oxabicyclo[3.2.1]octan-7-one (21)

$[α]^{20}_D$ −790 (c 1.0 $CHCl_3$); $^1$H NMR (500 MHz, $CDCl_3$) δ 0.086 (6H, s, 2×Si$CH_3$), 0.921 (9H, s, Si-t-Bu), 2.06 (1H, br t, J~11 Hz, 2α-H), 2.11 (1H, d, J=11.0 Hz, 8α-H), 2.14 (3H, s, O$CH_3$), 2.38 (1H, ddd, J=12.0, 7.5, 3.0 Hz, 2β-H), 3.34 (1H, ddd, J=11.0, 6.5, 3.0 Hz, 8β-H), 4.42 (1H, 3β-H), 5.15 (1H, d, J=6.5 Hz, 5α-H), 5.14 (1H, br s, one of C=$CH_2$), 5.25 (1H, d, J=1.5 Hz, one of C=$CH_2$); $^{13}$C NMR (125 MHz) δ −3.7, −3.5, 19.54, 22.57, 27.13, 42.36, 42.62, 66.07, 80.33, 112.18, 146.46, 170.61, 174.09; HRMS (ESI) exact mass calculated for $C_{16}H_{26}O_5SiNa$ ($M^++Na$) 349.1447. found 349.1451.

(3R,5R)-5-[(tert-Butyldimethylsilyl)oxy]-1,3-dihydroxy-4-methylene-cyclohexanecarboxylic acid methyl ester (22)

$[α]^{20}_D$ −71.30 (c 1.2 $CHCl_3$); $^1$H NMR (400 MHz, $CDCl_3$) δ 0.087 and 0.124 (each 3H, each s, 2×Si$CH_3$), 0.884 (9H, s, Si-t-Bu), 1.89 (1H, br t, J~12 Hz, 2β-H), 2.13 (2H, narr m, 6α- and 6β-H), 2.45 (1H, ddd, J=12.4, 4.7 Hz, 2.0 Hz, 2α-H), 3.77 (3H, s, COO$CH_3$), 4.70 (1H, narr m, 5β-H), 4.78 (1H, dd, J=11.1, 4.7 Hz, 3α-H), 5.01 (2H, s, one of C=$CH_2$), 5.02 (1H, s, —OH), 5.18 (1H, s, one of C=$CH_2$); $^{13}$C NMR (125 MHz) δ −5.43, −4.88, 17.79, 25.55, 40.74, 45.86, 52.61, 65.37, 75.07, 76.52, 108.09, 150.35, 173.71; HRMS (ESI) exact mass calculated for $C_{15}H_{28}O_5SiNa$ ($M^++Na$) 339.1598. found 339.1604.

(3R,5R)-3,5-Bis[(tert-butyldimethylsilyl)oxy]-1-hydroxy-4-methylene-cyclohexanecarboxylic acid methyl ester (23)

$[α]^{20}_D$ −31.50 (c 1.0 $CHCl_3$); $^1$H NMR (400 MHz, $CDCl_3$) δ 0.084, 0.094, and 0.119 (3H, 3H and 6H, each s, 4×Si$CH_3$), 0.892 and 0.922 (9H and 9H, each s, 2×Si-t-Bu), 1.82 (1H, t, J~12 Hz, 6β-H), 2.10 (2H, narr m, 2α- and 2β-H), 2.31 (1H, dd, J=12.4, 5.0 Hz, 6α-H), 3.75 (3H, s, COO$CH_3$), 4.69 (1H, narr m, 3β-H), 4.77 (1H, dd, J=11.2, 5.0 Hz, 5α-H), 4.95 (2H, s, one of C=$CH_2$ and OH), 5.16 (1H, s, one of C=$CH_2$); $^{13}$C NMR (100 MHz) δ −5.41, −5.05, −4.94, −4.90, 17.75, 18.17, 25.54, 25.76, 40.78, 46.53, 52.45, 65.93, 75.15, 108.43, 150.18, 173.72; HRMS (ESI) exact mass calculated for $C_{21}H_{42}O_5Si_2Na$ ($M^++Na$) 453.2469. found 453.2458.

(3R,5R)-3,5-Bis[(tert-butyldimethylsilyl)oxy]-4-methylene-cyclohex-1-enecarboxylic acid methyl ester (24)

$[α]^{20}_D$ −106° (c 1.0 $CHCl_3$); $^1$H NMR (500 MHz, $CDCl_3$) δ 0.057, 0.075, 0.099, and 0.129 (each 3H, each s, 4×Si$CH_3$), 0.885 and 0.917 (9H and 9H, each s, 2×Si-t-Bu), 2.33 (1H, dd, J=17.5, 6.0 Hz, 6α-H), 2.68 (1H, ddd, J=17.5, 3.0, 2.0 Hz, 6β-H), 3.74 (3H, s, COO$CH_3$), 4.57 (1H, t, J~5 Hz, 5β-H), 4.92 (1H, br s, 3α-H), 5.03 and 5.09 (1H and 1H, each s, C=$CH_2$), 6.75 (1H, narr m, 2-H); $^{13}$C NMR (125 MHz) δ −5.03, −4.91, −4.83, −4.78, 18.17, 18.26, 25.74, 25.80, 36.71, 51.87, 68.93, 69.46, 108.82, 129.28, 139.63, 148.78, 167.27; HRMS (ESI) exact mass calculated for $C_{21}H_{40}O_4Si_2Na$ ($M^++Na$) 435.2363. found 435.2364.

(3aR,4R,6R,7aR)-4,6-Bis[(tert-butyldimethylsilyl)oxy]-5-methylene-3,3a,4,5,6,7-hexahydro-indazole-7a-carboxylic Acid Methyl Ester (25)

$[α]^{20}_D$ −142° (c 1.0 $CHCl_3$); $^1$H NMR (500 MHz, $CDCl_3$) δ 0.012, 0.052, 0.056, and 0.096 (each 3H, each s, 4×Si$CH_3$), 0.857 and 0.921 (9H and 9H, each s, 2×Si-t-Bu), 1.28 (1H, dd, J=14.0, 2.9 Hz, 7β-H), 2.85 (1H, dd, J=14.0, 4.4 Hz, 7α-H), 2.92 (1H, m, 3α-H), 3.84 (3H, s, COO$CH_3$), 4.05 (1H, dd, J=17.7, 10.0 Hz, 3-$H_S$), 4.38 (1H, t, J~3.5 Hz, 6α-H), 4.75 (1H, dd, J=17.7, 7.9 Hz, 3-$H_R$), 4.90 (1H, d, J=6.6 Hz, 4β-H), 4.97 and 5.10 (1H and 1H, each s, C=$CH_2$); $^{13}$C NMR (125 MHz) δ −5.16, −5.08, −4.95, 17.96, 18.14, 25.52, 25.71, 38.17, 41.95, 52.95, 66.85, 72.17, 94.55, 110.41, 147.26, 170.35; HRMS (ESI) exact mass calculated for $C_{22}H_{42}O_4N_2Si_2Na$ ($M^++Na$) 477.2581. found 477.2573.

[(3'R,5'R)-3',5'-Bis[(tert-butyldimethylsilyl)oxy]-2'-methyl-4'-methylene-cyclohex-1'-enyl]-methanol (26)

$[α]^{20}_D$ −89° (c 1.0 $CHCl_3$); $^1$H NMR (400 MHz, $CDCl_3$) δ 0.043, 0.070, 0.081, and 0.125 (each 3H, each s, 4×Si$CH_3$), 0.879 and 0.919 (9H and 9H, each s, 2×Si-t-Bu), 1.76 (3H, s, 2'-$CH_3$), 2.10 (1H, dd, J=16.1, 9.6 Hz, 6β-H), 2.58 (1H, dd, J=16.1, 6.0 Hz, 6α-H), 4.11 (2H, s, C$H_2$—OH), 4.35 (1H, s, 3β-H), 4.57 (1H, br t, J~8 Hz, 5α-H), 4.90 and 5.15 (1H and 1H, each s, C=$CH_2$); $^{13}$C NMR (100 MHz) δ −4.86, −4.82, −4.69, 15.89, 18.17, 18.22, 25.83, 25.86, 40.30, 62.86, 67.69, 76.34, 107.62, 131.14, 132.30, 151.13; HRMS (ESI) exact mass calculated for $C_{21}H_{42}O_3Si_2Na$ ($M^+$+Na) 421.2570. found 421.2572.

[(1'S,3'R,5'R,6'R)-3,5-Bis[(tert-butyldimethylsilyl)oxy]-4'-methylene-bicyclo[4.1.0]hept-1-yl]methanol (27)

$^1$H NMR (400 MHz, CDCl$_3$) δ 0.053, 0.073, 0.087, and 0.103 (each 3H, each s, 4×SiCH$_3$), 0.42 (1H, t, J~5.5 Hz, 7'-H$_R$), 0.65 (1H, dd, J=9.0, 4.8 Hz, 7-H$_S$), 0.900 and 0.930 (9H and 9H, each s, 2×Si-t-Bu), 1.29 (1H, dt, J~9 and 6.5 Hz, 6'β-H), 1.76 (1H, dd, J=14.4, 2.9 Hz, one of 2'-H$_2$), 2.15 (1H, dd, J=14.4, 3.0 Hz, one of 2'-H$_2$), 2.22 (1H, t, J~4.7 Hz, OH), 2.84 (1H, dd, J=10.1, 4.6 Hz, one of C$\underline{H}_2$—OH), 3.65 (1H, dd, J=10.1, 4.7 Hz, one of C$\underline{H}_2$—OH), 4.31 (1H, t, J=2.9 Hz, 3'α-H), 4.99 (1H, br d, J 7 Hz, 5'β-H), 4.91 and 5.01 (1H and 1H, each s, C=CH$_2$); HRMS (ESI) exact mass calculated for $C_{21}H_{42}O_3Si_2Na$ ($M^+$+Na) 421.2570. found 421.2565.

(3R,5R)-3,5-Bis[(tert-butyldimethylsilyl)oxy]-2-methyl-4-methylene-cyclohex-1-enecarbaldehyde (28)

$[\alpha]^{20}_D$ −112° (c 1.0 CHCl$_3$); $^1$H NMR (400 MHz, CDCl$_3$) δ 0.066, 0.085, 0.094, and 0.168 (each 3H, each s, 4×SiCH$_3$), 0.908 (18H, s, 2×Si-t-Bu), 2.02 (1H, dd, J=17.0, 7.1 Hz, 6β-H), 2.20 (3H, s, CH$_3$), 2.78 (1H, dd, J=17.0, 5.5 Hz, 6α-H), 4.52 (1H, t, J~6.5 Hz, 5α-H), 4.58 (1H, s, 3β-H), 4.99 and 5.21 (1H and 1H, each s, C=CH$_2$), 10.11 (1H, s, CHO); $^{13}$C NMR (100 MHz) δ −4.94, −4.81, −4.15, 14.99, 18.13, 25.73, 25.80, 35.16, 67.51, 75.93, 108.97, 132.40, 149.55, 153.67, 191.66; HRMS (ESI) exact mass calculated for $C_{21}H_{40}O_3Si_2Na$ ($M^+$+Na) 419.2414. found 419.2417.

(3R,5R)-3,5-Bis[(tert-butyldimethylsilyl)oxy]-1-ethynyl-2-methyl-4-methylene-cyclohexene (14)

$[\alpha]^{20}_D$ −102° (c 1.0 CHCl$_3$); $^1$H NMR (400 MHz, CDCl$_3$) δ 0.060, 0.067, 0.078, and 0.126 (each 3H, each s, 4×SiCH$_3$), 0.880 and 0.913 (9H and 9H, each s, 2×Si-t-Bu), 1.95 (3H, s, CH$_3$), 2.15 (1H, br m, 6β-H), 2.55 (1H, dd, J=17.5, 6.3 Hz, 6α-H), 3.07 (1H, s, ≡CH), 4.46 (1H, s, 3β-H), 4.55 (1H, ddt, J=8.8, 6.3, ca. 2 Hz, 5α-H), 4.94 (1H, br s, one of C=CH$_2$), 5.16 (1H, t, J=1.9 Hz, one of C=CH$_2$); $^{13}$C NMR (100 MHz) δ −4.91, −4.78, −4.20, 18.12, 18.21, 25.74, 25.81, 41.88, 67.02, 74.79, 79.97, 83.26, 108.33, 114.71, 143.62, 150.07; HRMS (ESI) exact mass calculated for $C_{22}H_{40}O_2Si_2Na$ ($M^+$+Na) 415.2465. found 415.2455.

1α,3β-Bis[(tert-butyldimethylsilyl)oxy]-2-methylene-25-[(triethylsilyl)oxy]-9,10-secocholesta-5(10),8-dien-6-yne (29)

$^1$H NMR (400 MHz, CDCl$_3$) δ 0.051, 0.062, 0.072, and 0.116 (each 3H, each s, 4×SiCH$_3$), 0.562 (6H, q, J=7.8 Hz, 3×SiCH$_2$), 0.698 (3H, s, 18-H$_3$), 0.870 and 0.912 (9H and 9H, each s, 2×Si-t-Bu), 0.918 (3H, d, J=6.1 Hz, 21-H$_3$), 0.945 (9H, t, J=7.8 Hz, 3×SiCH$_2$C$\underline{H}_3$), 1.18 (6H, s, 26- and 27-H$_3$), 1.92 (3H, s, CH$_3$), 2.53 (1H, dd, J=16.6, 6.0 Hz), 4.45 (1H, s, 1β-H), 4.56 (1H, t, J~7.5 Hz, 3α-H), 4.91 and 5.14 (1H and 1H, each s, C=CH$_2$), 5.97 (1H, narr m, 9-H); HRMS (ESI) exact mass calculated for $C_{46}H_{84}O_3Si_3Na$ ($M^+$+Na) 791.5626. found 791.5637.

(20S)-1α,3-Bis[(tert-butyldimethylsilyl)oxy]-2-methylene-25-[(triethylsilyl)oxy]-9,10-secocholesta-5(10),8-dien-6-yne (30)

$^1$H NMR (500 MHz, CDCl$_3$) δ 0.051, 0.062, 0.074, and 0.117 (each 3H, each s, 4×SiCH$_3$), 0.561 (6H, q, J=8.0 Hz, 3×SiCH$_2$), 0.697 (3H, s, 18-H$_3$), 0.872 and 0.913 (9H and 9H, each s, 2×Si-t-Bu), 0.93 (3H, 21-H$_3$), 0.942 (9H, t, J=8.0 Hz, 3×SiCH$_2$C$\underline{H}_3$), 1.186 (6H, s, 26- and 27-H$_3$), 1.92 (3H, s, CH$_3$), 2.53 (1H, dd, J=16.0, 7.5 Hz), 4.46 (1H, s, 1β-H), 4.56 (1H, t, J~7 Hz, 3α-H), 4.91 and 5.14 (1H and 1H, each s, C=CH$_2$), 5.97 (1H, narr m, 9-H); HRMS (ESI) exact mass calculated for $C_{46}H_{84}O_3Si_3Na$ ($M^+$+Na) 791.5626. found 791.5638.

1α,3β-Bis[(tert-butyldimethylsilyl)oxy]-2-methylene-9,10-secocholesta-5(10),8-dien-6-yne (31)

$^1$H NMR (500 MHz, CDCl$_3$) δ 0.051, 0.062, 0.073, and 0.117 (each 3H, each s, 4×SiCH$_3$), 0.695 (3H, s, 18-H$_3$), 0.867 (6H, d, J=7.0 Hz, 26- and 27-H$_3$), 0.870 and 0.912 (9H and 9H, each s, 2×Si-t-Bu), 0.933 (3H, d, J=6.5 Hz, 21-H$_3$), 1.924 (3H, s, CH$_3$), 2.54 (1H, dd, J=16.5, 7.5 Hz), 4.45 (1H, s, 1β-H), 4.54 (1H, t, J~7 Hz, 3α-H), 4.91 and 5.15 (1H and 1H, each s, C=CH$_2$), 5.96 (1H, narr m, 9-H); $^{13}$C NMR (125 MHz, CDCl$_3$) δ −4.91, −4.88, −4.77, −4.17, 11.03, 18.12, 18.20, 18.70, 19.10, 22.63, 22.54, 22.81, 23.83, 24.16, 25.75, 25.84, 27.99, 35.86, 36.01, 36.16, 39.44, 41.80, 42.26, 50.06, 54.68, 67.13, 75.13, 87.57, 92.83, 107.96, 116.12, 122.47, 133.57, 140.52, 150.46; HRMS (ESI) exact mass calculated for $C_{40}H_{70}O_2Si_2Na$ ($M^+$+Na) 661.4812. found 661.4823.

(20S)-1α,3β-Bis[(tert-butyldimethylsilyl)oxy]-2-methylene-9,10-secocholesta-5(10),8-dien-6-yne (32)

$^1$H NMR (500 MHz, CDCl$_3$) δ 0.050, 0.062, and 0.071 (3H, 3H, 6H, each s, 4×SiCH$_3$), 0.694 (3H, s, 18-H$_3$), 0.839 (3H, d, J=6.5 Hz, 21-H$_3$), 0.868 (6H, d, J=6.5 Hz, 26- and 27-H$_3$), 0.870 and 0.912 (9H and 9H, each s, 2×Si-t-Bu), 1.924 (3H, s, CH$_3$), 2.53 (1H, dd, J=16.0, 7.5 Hz), 4.45 (1H, s, 1β-H), 4.54 (1H, t, J~7 Hz, 3α-H), 4.91 and 5.14 (1H and 1H, each s, C=CH$_2$), 5.96 (1H, narr m, 9-H); $^{13}$C NMR (125 MHz, CDCl$_3$) δ −4.91, −4.88, −4.78, −4.19, 11.23, 18.12, 18.23, 18.61, 19.11, 22.63, 22.73, 23.85, 24.07, 25.23, 25.75, 25.80, 27.92, 28.06, 35.55, 35.68, 35.85, 39.39, 41.82, 42.26, 50.12, 54.31, 67.13, 75.13, 87.58, 92.83, 107.97, 116.11, 122.49, 133.51, 140.54, 150.46; HRMS (ESI) exact mass calculated for $C_{40}H_{70}O_2Si_2Na$ ($M^+$+Na) 661.4812. found 661.4813.

1α-[(tert-Butyldimethylsilyl)oxy]-2-methylene-25-[(triethylsilyl)oxy]-vitamin D$_3$ tert-butyldimethylsilyl ether (37)

$^1$H NMR (500 MHz, CDCl$_3$) δ 0.055, 0.059, 0.074, and 0.082 (each 3H, each s, 4×SiCH$_3$), 0.538 (3H, s, 18-H$_3$), 0.562 (6H, q, J=7.5 Hz, 3×SiCH$_2$), 0.890 (18H, s, 2×Si-t-Bu), 0.922 (3H, d, J=6.5 Hz, 21-H$_3$), 0.945 (9H, t, J=7.5, 3×SiCH$_2$C$\underline{H}_3$), 1.18 (6H, s, 26- and 27-H$_3$), 2.26 (1H, dd, J=13.0, 7.0 Hz, 4β-H), 2.50 (1H, dd, J=13.0, 4.5 Hz, 4α-H), 2.83 (1H, br d, J=13.5 Hz, 9β-H), 4.55 (1H, m, 3α-H), 4.72 (1H, s, 1β-H), 4.85, 4.95, 4.98 and 5.23 (each 1H, each s, 2×C=CH$_2$), 6.04 and 6.29 (1H and 1H, each d, J=11.0 Hz, 7- and 6-H); HRMS (ESI) exact mass calculated for C$_{46}$H$_{86}$O$_3$Si$_3$Na (M$^+$+Na) 793.5782. found 793.5778.

(20S)-1α-[(tert-Butyldimethylsilyl)oxy]-2-methylene-25-[(triethylsilyl)oxy]-vitamin D$_3$ tert-butyldimethylsilyl ether (38)

$^1$H NMR (500 MHz, CDCl$_3$) δ 0.054, 0.059, 0.069, and 0.082 (each 3H, each s, 4×SiCH$_3$), 0.534 (3H, s, 18-H$_3$), 0.563 (6H, q, J=8.0 Hz, 3×SiCH$_2$), 0.883 (3H, d, J=6.5 Hz, 21-H$_3$), 0.891 (18H, s, 2×Si-t-Bu), 0.944 (9H, t, J=8.0 Hz, 3×SiCH$_2$CH$_3$), 1.187 (6H, s, 26- and 27-H$_3$), 2.26 (1H, dd, J=12.5, 7.0 Hz, 4β-H), 2.50 (1H, dd, J=12.5, 4.5 Hz, 4α-H), 2.83 (1H, br d, J=12.5 Hz, 9β-H), 4.55 (1H, dd, J=7.0, 4.5 Hz, 3α-H), 4.72 (1H, s, 1β-H), 4.85, 4.95, 4.99, and 5.23 (each 1H, each s, 2×C=CH$_2$), 6.04 and 6.29 (1H and 1H, each d, J=11.0 Hz, 7- and 6-H); HRMS (ESI) exact mass calculated for C$_{46}$H$_{86}$O$_3$Si$_3$Na (M$^+$+Na) 793.5782. found 793.5788.

1α-[(tert-Butyldimethylsilyl)oxy]-2-methylene-vitamin D$_3$ tert-butyldimethylsilyl Ether (39)

$^1$H NMR (500 MHz, CDCl$_3$) δ 0.055, 0.059, 0.071, and 0.081 (each 3H, each s, 4×SiCH$_3$), 0.535 (3H, s, 18-H$_3$), 0.864 and 0.870 (3H and 3H, each d, J=7.0 Hz, 26- and 27-H$_3$), 0.889 and 0.891 (9H and 9H, each s, 2×Si-t-Bu), 0.919 (3H, d, J=6.5 Hz, 21-H$_3$), 2.27 (1H, dd, J=12.5, 7.0 Hz, 4J-H), 2.51 (1H, dd, J=12.5, 4.5 Hz, 4α-H), 2.83 (1H, br d, J=12.5 Hz, 9β-H), 4.55 (1H, dd, J=7.0, 4.5 Hz, 3α-H), 4.72 (1H, s, 1β-H), 4.85, 4.95, 4.98, and 5.23 (each 1H, each s, 2×C=CH$_2$), 6.04 and 6.29 (1H and 1H, each d, J=11.0 Hz, 7- and 6-H); $^{13}$C NMR (125 MHz, CDCl$_3$) δ −4.96, −4.86, −4.64, 1.02, 11.96, 18.19, 18.25, 18.83, 22.12, 22.55, 22.82, 23.53, 23.88, 25.74, 25.82, 27.71, 28.01, 29.69, 36.14, 39.48, 40.58, 45.79, 46.98, 56.33, 56.57, 67.93, 71.36, 106.44, 111.16, 117.78, 123.78, 134.18, 141.60, 147.98, 152.41; HRMS (ESI) exact mass calculated for C$_{40}$H$_{72}$O$_2$Si$_2$Na (M$^+$+Na) 663.4968. found 663.4969.

(20S)-1α-[(tert-Butyldimethylsilyl)oxy]-2-methylene-vitamin D$_3$ tert-butyldimethylsilyl ether (40)

$^1$H NMR (500 MHz, CDCl$_3$) δ 0.055, 0.059, 0.071, and 0.082 (each 3H, each s, 4×SiCH$_3$), 0.531 (3H, s, 18-H$_3$), 0.832 (3H, d, J=6.5 Hz, 21-H$_3$), 0.868 (6H, d, J=6.5 Hz, 26- and 27-H$_3$), 0.890 (18H, s, 2×Si-t-Bu), 2.27 (1H, dd, J=12.5, 7.0 Hz, 4β-H), 2.51 (1H, dd, J=12.5, 4.5 Hz, 4α-H), 2.83 (1H, br d, J=12.5 Hz, 9β-H), 4.55 (1H, dd, J=7.0, 4.5 Hz, 3α-H), 4.72 (1H, s, 1β-H), 4.85, 4.95, 4.98, and 5.23 (each 1H, each s, 2×C=CH$_2$), 6.04 and 6.29 (1H and 1H, each d, J=11.0 Hz, 7- and 6-H); $^{13}$C NMR (125 MHz, CDCl$_3$) δ −5.09, −4.96, −4.86, 1.02, 12.19, 18.19, 18.33, 18.62, 22.01, 22.65, 22.74, 23.54, 23.97, 25.75, 25.86, 27.45, 28.07, 28.93, 29.07, 35.57, 35.77, 45.83, 46.99, 56.18, 56.37, 67.60, 71.37, 106.45, 111.15, 117.80, 123.78, 134.20, 141.57, 147.98, 152.40; HRMS (ESI) exact mass calculated for C$_{40}$H$_{72}$O$_2$Si$_2$Na (M$^+$+Na) 663.4968. found 663.4968.

1α,25-dihydroxy-2-methylene-vitamin D$_3$ (8)

UV (EtOH) λ$_{max}$ 269.0 nm; $^1$H NMR (500 MHz, CDCl$_3$) δ 0.551 (3H, s, 18-H$_3$), 0.939 (3H, d, J=6.5 Hz, 21-H$_3$), 1.218 (6H, s, 26- and 27-H$_3$), 2.39 (1H, dd, J=13.3, 6.5 Hz, 4β-H), 2.67 (1H, dd, J=13.3, 3.8 Hz, 4α-H), 2.83 (1H, br d, J=12.7 Hz, 9β-H), 4.61 (1H, m, 3α-H), 4.87 (1H, br s, 1β-H), 5.02, 5.11, 5.16, and 5.39 (each 1H, each s, 2×C=CH$_2$), 6.07 and 6.44 (1H and 1H, each d, J=11.5 Hz, 7- and 6-H); HRMS (ESI) exact mass calculated for C$_{28}$H$_{44}$O$_3$Na (M$^+$+Na) 451.3188. found 451.3177.

(20S)-1α,25-dihydroxy-2-methylene-vitamin D$_3$ (9)

UV (EtOH) λ$_{max}$ 270.0 nm; $^1$H NMR (500 MHz, CDCl$_3$) δ 0.549 (3H, s, 18-H$_3$), 0.852 (3H, d, J=6.5 Hz, 21-H$_3$), 1.215 (6H, s, 26- and 27-H$_3$), 2.39 (1H, dd, J=13.7, 6.5 Hz, 4β-H), 2.66 (1H, dd, J=13.7, 4.0 Hz, 4α-H), 2.83 (1H, br d, J=12.0 Hz, 9β-H), 4.61 (1H, ~q, J=5.5 Hz, 3α-H), 4.87 (1H, br d, J~5.5 Hz, 1β-H), 5.018, 5.108, 5.159, and 5.397 (each 1H, each s, 2×C=CH$_2$), 6.07 and 6.43 (1H and 1H, each d, J=11.5 Hz, 7- and 6-H); HRMS (ESI) exact mass calculated for C$_{28}$H$_{44}$O$_3$Na (M$^+$+Na) 451.3188. found 451.3174.

1α-hydroxy-2-methylene-vitamin D$_3$ (10)

UV (EtOH) λ$_{max}$ 270.0 nm; $^1$H NMR (500 MHz, CDCl$_3$) δ 0.548 (3H, s, 18-H$_3$), 0.864 and 0.869 (3H and 3H, each d, J=6.5 Hz, 26- and 27-H$_3$), 0.919 (3H, d, J=6.5 Hz, 21-H$_3$), 2.39 (1H, dd, J=13.5, 6.5 Hz, 4β-H), 2.66 (1H, dd, J=13.5, 4.0 Hz, 4α-H), 2.83 (1H, dd, J=12.5, 4.0 Hz, 9β-H), 4.61 (1H, narr m, 3α-H), 4.87 (1H, s, 1β-H), 5.02, 5.11, 5.16, and 5.40 (each 1H, each s, 2×C=CH$_2$), 6.07 and 6.44 (1H and 1H, each d, J=11.5 Hz, 7- and 6-H); $^{13}$C NMR (125 MHz, CDCl$_3$) δ 11.99, 18.81, 22.27, 22.55, 22.81, 23.61, 23.82, 27.61, 28.00, 29.11, 36.09, 39.47, 40.43, 45.56, 45.92, 56.35, 56.54, 71.19, 74.64, 108.24, 112.00, 116.92, 125.59, 131.96, 143.84, 146.67, 151.05; HRMS (ESI) exact mass calculated for C$_{28}$H$_4$O$_2$Na (M$^+$+Na) 435.3239. found 435.3241.

(20S)-1α-hydroxy-2-methylene-vitamin D$_3$ (11)

UV (EtOH) λ$_{max}$ 270.0 nm; $^1$H NMR (500 MHz, CDCl$_3$) δ 0.544 (3H, s, 18-H$_3$), 0.831 (3H, d, J=6.5 Hz, 21-H$_3$), 0.867 (6H, d, J=6.5 Hz, 26- and 27-H$_3$), 2.39 (1H, dd, J=13.2, 6.5 Hz, 4β-H), 2.66 (1H, dd, J=13.2, 4.0 Hz, 4α-H), 2.83 (1H, dd, J=12.5, 4.5 Hz, 9β-H), 4.61 (1H, narr m, 3α-H), 4.87 (1H, s, 1β-H), 5.02, 5.11, 5.16, and 5.40 (each 1H, each s, 2×C=CH$_2$), 6.07 and 6.44 (1H and 1H, each d, J=11.5 Hz, 7- and 6-H); $^{13}$C NMR (125 MHz, CDCl$_3$) δ 12.23, 18.59, 22.15, 22.63, 22.73, 23.61, 23.95, 27.34, 28.05, 29.12, 35.53, 35.75, 39.39, 40.33, 45.57, 45.95, 56.18, 56.38, 71.17, 74.66, 108.24, 112.03, 116.94, 125.58, 131.98, 143.80, 146.66, 151.05; HRMS (ESI) exact mass calculated for C$_{28}$H$_{44}$O$_2$Na (M$^+$+Na) 435.3239. found 435.3240.

(5E)-1α,25-dihydroxy-2-methylene-vitamin D$_3$ (12)

UV (EtOH) λ$_{max}$ 278.0 nm; $^1$H NMR (500 MHz, CDCl$_3$) δ 0.597 (3H, s, 18-H$_3$), 0.945 (3H, d, J=6.6 Hz, 21-H$_3$), 1.224 (6H, s, 26- and 27-H$_3$), 2.38 (1H, dd, J=14.0, 9.0 Hz, 4β-H), 2.86 (1H, br d, J=13.5 Hz, 9β-H), 2.93 (1H, dd, J=14.0, 4.5 Hz, 4α-H), 4.64 (1H, m, 3α-H), 4.89 (1H, br s, 1β-H), 5.05 and 5.15, 5.17, and 5.18 (each 1H, each s, 2×C=CH$_2$), 5.90 and 6.55 (1H and 1H, each d, J=11.5 Hz, 7- and 6-H); HRMS (ESI) exact mass calculated for C$_{28}$H$_{44}$O$_3$Na (M$^+$+Na) 451.3188. found 451.3197.

(5E)-(20S)-1α,25-dihydroxy-2-methylene-vitamin D$_3$ (13)

UV (EtOH) λ$_{max}$ 278.0 nm; $^1$H NMR (500 MHz, CDCl$_3$) δ 0.567 (3H, s, 18-H$_3$), 0.869 (3H, d, J=6.0 Hz, 21-H$_3$), 1.217 (6H, s, 26- and 27-H$_3$), 2.38 (1H, dd, J=14.0, 9.0 Hz, 4β-H), 2.86 (1H, br d, J=13.5 Hz, 9β-H), 2.93 (1H, dd, J=14.0, 4.5 Hz, 4α-H), 4.64 (1H, m, 3α-H), 4.89 (1H, d, J=4.5 Hz, 1β-H), 5.05 and 5.15 (each 1H, each s, 2×C=CH$_2$), 5.17 and 5.18 (each 1H, each d, J=1 Hz, 2×C=CH$_2$), 5.90 and 6.55 (1H and 1H, each d, J=11.5 Hz, 7- and 6-H); HRMS (ESI) exact mass calculated for C$_{28}$H$_{44}$O$_3$Na (M$^+$+Na) 451.3188. found 451.3193.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of references are made herein. The cited references are incorporated by reference herein in their entireties. In the event that there is an inconsistency between a definition of a term in the specification as compared to a definition of the term in a cited reference, the term should be interpreted based on the definition in the specification.

REFERENCES

[1] (a) Norman, A. W. Vitamin D, the calcium homeostatic hormone. Academic Press, New York, 1979. (b) Feldman, D.; Pike, J. W.; Adams, J. S., Eds. Vitamin D, 3rd ed.; Elsevier Academic Press: San Diego, Calif., 2011.

[2] (a) Jones, G.; Strugnell, S. A.; DeLuca, H. F. Current understanding of the molecular actions of vitamin D. Physiol. Rev. 1998, 78, 1193-1231. (b) Haussler, M. R.; Whitfield, G. K.; Kaneko, I.; Haussler, C. A.; Hsieh, D.; Hsieh, J. C.; Jurutka, P. W. Molecular mechanisms of vitamin D action. Calcif Tissue Int. 2013, 92, 77-98.

[3] (a) Bouillon, R; Okamura, W. H.; Norman, A. W. Structure-function relationships in the vitamin D endocrine system. Endocr. Rev. 1995, 16, 200-257. (b) Okamura, W. H.; Zhu, G. D. Chemistry and design: structural biology of vitamin D action. In: Feldman, D.; Glorieux, F. H.; Pike, J. W. (Eds.), Vitamin D: Academic Press, New York, 1997, 937-971. (c) Binderup, L.; Binderup. E.; Godtfredsen, W. O. Development of new vitamin D analogs. In: Feldman, D.; Glorieux, F. H.; Pike, J. W. (Eds.), Vitamin D: Academic Press, New York, 1997, 1027-1043.

[4] Sicinski, R. R.; Prahl, J. M.; Smith, C. M.; DeLuca, H. F. New 1α,25-dihydroxy-19-norvitamin D$_3$ compounds of high biological activity: synthesis and biological evaluation of 2-hydroxymethyl, 2-methyl and 2-methylene analogues. J. Med. Chem. 1998, 41, 4662-4674.

[5] Shevde, N. K.; Plum, L. A.; Clagett-Dame, M.; Yamamoto, H.; Pike, J. W.; DeLuca, H. F. A potent analog of 1α,25-dihydroxyvitamin D$_3$ selectively induces bone formation. Proc. Natl. Acad. Sci. USA 2002, 99, 13487-13491. (b) Yamamoto, 1.; Shevde, N. K.; Warrier, A.; Plum. L. A.; DeLuca, H. F.; Pike, J. W.; 2-Methylene-19-nor-(20S)-1, 25-dihydroxyvitarnin 13 potently stimulates gene-specific DNA binding of the vitamin D receptor in osteoblasts. J. Biol. Chem. 2003, 278, 31756-31765.

[6] (a) Ke, H. Z.; Qi, H.; Crawford, D. T.; Simmons, H. A.; Xu, G.; Li, M.; Plum, L.; Clagett-Dame, M.; DeLuca, H. F.; Thompson, D. D.; Brown, T. A. A new vitamin D analog, 2MD, restores trabecular and cortical bone mass and strength in ovariectomized rats with established osteopenia. J. Bone Miner. Res. 2005, 20, 1742-1755. (b) Plum, L. A.; Fitzpatrick, L. A.; Ma, X.; Binklev, N.; Zella, J. B.; Clagett-Dame, M.; DeLuca, H. F. 2MD, a new anabolic agent for osteoporosis treatment. Osteoporos. Int. 2006, 17, 704-715. (c) DeLuca, H. F. The development of a bone- and parathyroid-specific analog of vitamin D: 2-methylene-19-nor-(20S)-1α,25-dihydroxyvitamin D$_3$. In: BoneKEy Reports, Article number 514 (2014).

[7] DeLuca, H. F.; Bedale, W.; Binkley, N.; Gallagher, J. C.; Bolognese, M.; Peacock, M.; Aloia, J.; Clagett-Dame, M.; Plum, L. The vitamin D analogue 2MD increases bone turnover but not BMD in postmenopausal women with osteopenia: Results of a 1-year phase 2 double-blind, placebo-controlled, randomized clinical trial. J. Bone Miner. Res. 2011, 26, 538-545.

[8] (a) Sicinski, R. R. 2-Alkylidene analogs of 19-nor-1α,25-(OH)$_2$D$_3$: Synthesis and biological activity. Polish J. Chem. 2006, 80, 573-585. (b) Glebocka, A.; Chiellini, G. A-Ring analogs of 1,25-dihydroxyvitamin D$_3$. Arch. Biochem. Biophys. 2012, 523, 48-57.

[9] Sibilska, I. K.; Barycka, K. M.; Sicinski, R. R.; Plum, L. A.; DeLuca, H. F. 1-Desoxy analog of 2MD: synthesis and biological activity of (20S)-25-hydroxy-2-methylene-19-norvitamin D$_3$. J. Steroid Biochem. Mol. Biol. 2010, 121, 51-55.

[10] DeLuca, H. F.; Sibilska, I. K.; Plum, L. A.; Clagett-Dame, M.; Sicinski, R. R. 3-Desoxy-2-methylene-19-nor-vitamin D analogs and their uses. U.S. Patent Appl. 2012/0322775 A1, Dec. 20, 2012.

[11] Sibilska, I. K.; Sicinski, R. R.; Plum, L. A.; DeLuca, H. F. Synthesis and biological activity of 25-hydroxy-2-methylene-vitamin D$_3$ compounds. J. Steroid Biochem. Mol. Biol. 2013, 136, 17-22.

[12] Sibilska, I. K.; Sicinski, R. R.; Ochalek, J. T.; Plum, L. A.; DeLuca, H. F. Synthesis and biological activity of 25-hydroxy-2-methylene-vitamin D$_3$ analogues monohydroxylated in the A-ring. J. Med. Chem. 2014, 57, 8319-8331.

[13] Sibilska, I. K.; Szybinski, M.; Sicinski, R. R.; Plum, L. A.; DeLuca, H. F. Highly potent 2-methylene analogs of 1α,25-dihydroxyvitamin D$_3$: Synthesis and biological evaluation. J. Steroid Biochem. Mol. Biol. 2013, 136, 17-22.

[14] Glebocka, A.; Sicinski, R. R.; Plum, L. A.; Clagett-Dame, M.; DeLuca, H. F. New 2-alkylidene 1α,25-dihydroxy-19-norvitamin D$_3$ analogues of high intestinal activity: synthesis and biological evaluation of 2-(3'-alkoxypropylidene) and 2-(3'-hydroxypropylidene) derivatives. J. Med. Chem. 2006, 49, 2909-2920.

[15] Desmaele, D.; Tanier, S. Nouvelle synthese du cycle a du 1S-hydroxycholecalciferol a partir de l'acide quinique. Tetrahedron Lett. 1985, 26, 4941-4944.

[16] (a) Gothelf, K. V.; Jorgensen, K. A. Asymmetric 1,3-dipolar cycloaddition reactions. Chem. Rev. 1998, 98, 863-909. (b) Padwa, A., Pearson, W. H., Eds. Synthetic applications of 1,3-dipolar cycloaddition chemistry toward heterocycles and natural products; An Interscience Publication John Wiley & Sons, Inc. Hoboken, N.J., 2003; Vol. 59, p. 539.

[17] (a) Sicinski, R. R.; Perlman, K. L.; DeLuca, H. F. Synthesis and biological activity of 2-hydroxy and 2-alkoxy analogues of 1α,25-dihydroxy-19-norvitamin D$_3$. J. Med. Chem. 1994, 37, 3730-3738. (b) Sicinski, R. R.; Prahl, J. M.; Smith, C. M.; DeLuca, H. F. New 1α,25-dihydroxy-19-norvitamin D$_3$ compounds of high biological activity: Synthesis and biological evaluation of 2-hydroxymethyl, 2-methyl and 2-methylene analogues.

J. Med. Chem. 1998, 41, 4662-4674. (c) Maestro, M. A.; Sardina, F. J.; Castedo, L.; Mourino, A. J. Org. Chem. 1991, 56, 3582-3587. (d) DeLuca, H. F.; Sicinski, R. R.; Grzywacz, P. K. (20S)-1α-hydroxy-2α-methyl and 20-methyl-19-nor-vitamin $D_3$ and their uses. U.S. Pat. No. 6,846,811 B2, Jan. 25, 2005.

[18] Hayashi, R.; Fernandez, S.; Okamura, W. H. An 8π electron electrocyclization leading to a 9,19-methano-bridged analogue of 1α,25-dihydroxyvitamin $D_3$. Org. Lett. 2002, 4, 851-854.

[19] Mascareñas, J. L.; Sarandeses, L. A.; Castedo, L.; Mourifio, A. Palladium-catalysed coupling of vinyl triflates with enynes and its application to the synthesis of 1α,25-dihydroxyvitamin $D_3$. Tetrahedron 1991, 47, 3485-3498.

[20] Verloop, A.; Koevoet, A. L.; Van Moorselaar, R.; Havinga, E. Studies on vitamin D and related compounds IX: Remarks on the iodine-catalyzed isomerisations of vitamin D and related compounds. Rec. Trav. Chim. 1959, 78, 1004-1014.

[21] Chen, Y.; Gao, L.-J.; Murad, I.; Verstuyf, A.; Verlinden, L.; Verboven, C.; Bouillon, R.; Viterbo, D.; Milanesio, M.; Van Haver, D.; Vandewalle, M.; De Clercq, P. J. Synthesis, biological activity, and conformational analysis of CD-ring modified trans-decalin 1α,25-dihydroxyvitamin D analogs. Org. Biomol. Chem. 2003, 1, 257-267.

[22] (a) Glebocka, A.; Sicinski, R. R.; Plum, L. A.; Clagett-Dame, M.; DeLuca, H. F. New 2-alkylidene 1α,25-dihydroxy-19-norvitamin $D_3$ analogues of high intestinal activity: synthesis and biological evaluation of 2-(3'-alkoxypropylidene) and 2-(3'-hydroxypropylidene) derivatives. J. Med. Chem. 2006, 49, 2909-2920. (b) Chiellini, G.; Grzywacz, P.; Plum, L. A.; Barycki, R.; Clagett-Dame, M.; DeLuca, H. F. Synthesis and biological properties of 2-methylene-19-nor-25-dehydro-1α-hydroxyvitamin $D_3$-26,23-lactones-weak agonists. Bioorg. Med. Chem. 2008, 16, 8563-8573.

[23] Suda, T.; DeLuca, H. F.; Tanaka, Y. Biological activity of 25-hydroxyergocalciferol in rats. J. Nutr. 1970, 100, 1049-1052.

We claim:

1. A compound having a formula:

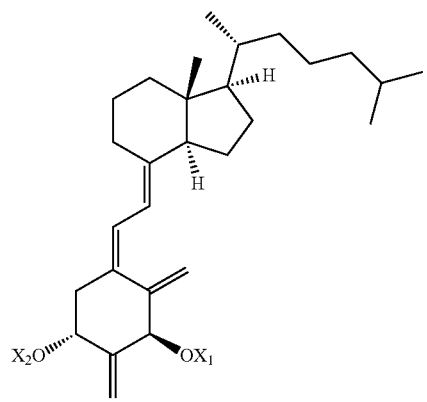

wherein:

$X_1$, and $X_2$, which may be the same or different, are each selected from hydrogen or a hydroxy-protecting group.

2. The compound of claim 1, wherein $X_1$ and $X_2$ are t-butyldimethylsilyl.

3. The compound of claim 1, wherein $X_1$ and $X_2$ are hydrogen.

4. The compound of claim 1 having a formula:

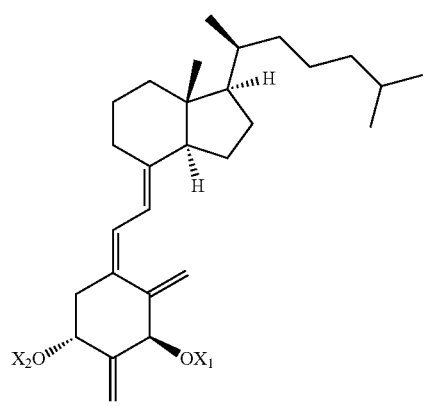

and called 1α-hydroxy-2-methylene-vitamin $D_3$.

5. The compound of claim 1 having a formula:

and called (20S)-1α-hydroxy-2-methylene-vitamin $D_3$.

6. A pharmaceutical composition containing an effective amount of the compound of claim 1 and a pharmaceutically acceptable excipient.

7. A method for increasing bone strength in a patient in need thereof, the method comprising administering to the patient an effective amount of the compound of claim 1.

* * * * *